(12) United States Patent
Lu et al.

(10) Patent No.: US 6,462,173 B1
(45) Date of Patent: *Oct. 8, 2002

(54) INHIBITORS OF PHOSPHOSERINE AND PHOSPHOTHREONINE-PROLINE-SPECIFIC ISOMERASES

(75) Inventors: Kun Ping Lu, Newton; Lewis Cantley, Cambridge; Michael Yaffe, Somerville, all of MA (US); Gunter Fischer, Halle (DE)

(73) Assignees: Max-Planck-Gesellschaft zur Forderung der, Berlin (DE); Beth Israel Deaconess Medical Center, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/988,842

(22) Filed: Dec. 11, 1997

Related U.S. Application Data
(60) Provisional application No. 60/058,164, filed on Sep. 8, 1997.

(51) Int. Cl.$^7$ ................................................. C07K 7/00
(52) U.S. Cl. ...................... 530/328; 530/329; 530/330; 530/331; 514/17; 514/18; 514/19; 562/567; 562/570; 548/535
(58) Field of Search .......................... 548/535; 562/567, 562/570; 514/17–19; 530/328, 329, 330, 331

(56) References Cited

U.S. PATENT DOCUMENTS

| | | | | |
|---|---|---|---|---|
| 4,444,682 A | * | 4/1984 | Rivier | 260/112.5 |
| 4,490,364 A | * | 12/1984 | Rivier | 424/177 |
| 4,584,377 A | | 4/1986 | Yokoi et al. | 546/15 |
| 4,612,132 A | | 9/1986 | Wollenberg et al. | 252/51.5 |
| 4,673,678 A | | 6/1987 | Misra | 514/278 |
| 5,013,722 A | * | 5/1991 | Danho | 514/16 |
| 5,166,208 A | | 11/1992 | Kelly et al. | 514/278 |
| 5,532,167 A | | 7/1996 | Cantley et al. | 436/89 |
| 5,601,985 A | * | 2/1997 | Trojanowski | 435/7.1 |
| 5,643,873 A | | 7/1997 | Barrett et al. | 514/12 |
| 5,654,276 A | | 8/1997 | Barrett et al. | 514/13 |

FOREIGN PATENT DOCUMENTS

WO     WO 97/17986     5/1997

OTHER PUBLICATIONS

Chem. Abstr. 126, 340373, 1997.*
Chem. Abstr. 118, 186454, 1993.*
Derwent Abstract of JP 91/0,146,477, 1992.*
Izumi, T., and Maller, J.L., "Elimination of cdc2 Phosphorylation Sites in the cdc25 Phosphatase Blocks Initiation of M–Phase," *Mol. Biol. of the Cell*, 4:1337–1350 (1993).

Kofron, J.L., et al., "Determination of Kinetic Constants for Peptidyl Prolyl Cis–Trans Isomerases by an Improved Spectrophotometric Assay," *Biochemistry*, 30:6127–6134 (1991).
Kuang, J., et al., "cdc25 Is One of the MPM–2 Antigens Involved in the Activation of Maturation–Promoting Factor," *Mol. Biol. of the Cell.*, 5:135–145 (1994).
Rahfeld, J–U., et al., "confirmation of the Existence of a Third Family Among Peptidly–Prolyl cis/trans Isomerases. Amino Acid Sequence and Recombinant Production of Parvulin," *FEBS Letters*, 352:180–184 (1994)..
Ying, J–Y., et al., "Theonine Phosphorylation is Associated with Mitosis in HeLa Cells," *FEB*, 249(2):389–395 (1989).
Ogg, S., et al., "Purification of a Serine Kinase That Associates With and Phosphorylates Human Cdc25C on Serine 216," *J. Biol Chem.*, 269(48):30461–30469 (1994).
Kuang, J. and Ashorn, C.L., "At Least Two Kinases Phosphorlate the MPM–2 Epitope During Xenopus Oocyte Maturation," *J. Cell Biol.*, 123(4):859–868 (1993).
Murray, A.W., "Cell Cycle Extracts," Chapter 30, In *Methods Cell Biol*, 36 (Academic Press Inc.)pp. 851–605 (1991).
Nicholls, A., et al., "Protein Folding and Association: Insights From the Interfacial and Thermodynamic Properties of Hydrocarbons," *Proteins*, 11:281–296 (1991).
Rudd, K.E., et al., "A New Family of Peptidyl–Prolyl Isomerases," *TIBS*, 20:12–13 (1995).
Schmid, F.X., "Prolyl Isomerases Join the Fold," *Curr. Biol.*, 5(9):993–994 (1995).
Schutkowski, M., et al., "Inhibition of Peptidyl–Prolyl cis/trans Isomaerase Activity by Substrate Analog Structures; Thioxo Tetrapeptide–4–Nitroanilides," *Biochemistry*, 34:13016–13026 (1995).
Stukenberg, P.T., et al., "Systematic Identification of Mitotic Phosphoproteins," *Curr. Biol.*, 7:338–348 (1997).
Ziang, S.Y., et al., "The NIMA Protein Kinase in Hyperphosphorylated and Activated Downstream of the p34$^{cdc2}$/cyclin B: Coordination of Two mitosis Promoting Kinases," *EMBO J.*, 14:986994 (1995).
Fischer, G., "Peptidyl–Prolyl cis/trans Isomerases and Their Effectors," *Angew. Chem. Int. Ed. Engl.*, 33:1415–1436 (1994).

(List continued on next page.)

*Primary Examiner*—Christopher S. F. Low
*Assistant Examiner*—David Lukton
(74) *Attorney, Agent, or Firm*—Lahive & Cockfield, LLP; Elizabeth A. Hanley, Esq.; Cynthia L. Kanik, Esq.

(57) ABSTRACT

Inhibitors of phosphoserine- or posphothreonine-specific peptidyl prolyl isomerases are described. Such inhibitors include molecules that mimic the structure and conformation of the pSer/pThr-Pro peptide moiety of the isomerase substrate when the substrate is bound into the active site of the isomerase. For example, a protein, peptide or peptide mimetic including xSer/ThrY where x is a negatively charged tetra or pentavalent moiety and Y is a Pro or a Pro analog. Methods of inhibiting cell growth and methods of identifying phosphoserine- or phosphothreonine-proline specific peptidyl-prolyl isomerase inhibitors are also included in the invention.

19 Claims, 3 Drawing Sheets

OTHER PUBLICATIONS

Coleman, R. and Dunphy. W.G., "Cdc2 Regulatory Factors," *Curr. Opin. Biol.*, 6:877–882 (1994).

Peng, C–Y., et al., "Mitotic and $G^2$ Checkpoint Control: Regulation of 14–3–3 Protein Binding by Phosphorylation of Cdc25C on Serine–216," *Science*, 277:1501–1505 (1997).

Maleszka, R., et al., "The *Drosophila Melanogaster* dodo (dod) gene, Conserved in Humans, is Functionally Interchangeable with the ESS1 Cell Division gene of *Saccharomyces Cerevisiae*," *Proc. Natl. Acad. Sci. USA*, 93:447–451 (1996).

Hanes, S.D., et al., "Sequence and Mutational Analysis of ESS1, a Gene Essential for Growth in *Saccharomyces Cervisiae*," *Yeast*, 5:55–72 (1989).

Heintz, N., et al., "Regulation of Human Histone Gene Expression: Kinetics of Accumulation and Changes in the Rate of Synthesis and in the Half–Lives of Individual Histone mRNAs During the HeLa Cell Cycle," *Mol. and Cell. Biol.*, 3(4):539–550 (1983).

Davis, F.M., et al., "Monoclonal Antibodies to Mitotic Cells," *Proc. Natl. Acad. Sci. USA*, 80:2926–2930 (1983).

Razi, L., et al., "MPM–2 Antibody–Reactive Phosphorylations Can be Created in Detergent=Extracted Cells by Kinetochore–Bound and Soluble Kinases," *J. Cell Scinece*, 110:2013–2025 (1997).

Taagepera S., et al., "The MPM–2 Antibody Inhibits Mitogen–Activated Protein Kinase Activity by Binding to an Epitope Containing Phosphothreonin–183," *Mol. Biol. of Cell*, 5:1243–1251 (1994).

Westendorf, J.M., et al., "Cloning of cDNAs for M–Phase Phosphoproteins Recognized by the MPM2 Monoclonal Antibody and Determination of the Phosphorylated Epitope," *Proc. Natl. Acad. Sci. USA*, 91:714–718 (1994).

Lu, K.P., et al., "A Human Peptidyl–Prolyl Isomerase Essential for Regulation of Mitosis," *Nature*, 380:544–547 (1996).

Schreiber, S.L., "Chemistry and Biology of the Immunophilins and Their Immunosuppressive Ligands," *Science*, 251:283–287 (1991).

Kumagai, A. and Dunphy, W.G., "Purification and Molecular Cloning of Plx1, a Cdc25–Regulatory Kinase from Xenopus Egg Extracts," *Science*, 273:1377–1380 (1996).

Heald, R. and McKeon F., "Mutation of Phosphorylation Sites in Lamin A That Prevent Nuclear Lamina Disassembly in Mitosis," *Cell*, 61:579–589 (1990).

Blangy, A., et al., "Phosphorylation by $p34^{cdc2}$ Regulates Spindle Association of Human Eg5, a Kinesin–Related Motor Essential for Bipolar Spindle Formation In Vivo," *Cell*, 83:1159–1169 (1995).

Nurse, P., "Ordering S Phase and M Phase in the Cell Cycle," *Cell*, 79:547–550 (1994).

King, R.W., et al., "Mitosis in Transition," *Cell*, 79:563–571 (1994).

Solomon, M.J., et al., "Cyclin Activation of $p34^{cdc2}$," *Cell*, 63:1013–1024 (1990).

Saragovi, H.U., et al., "Loops and Secondary Structure Mimetics: Development and Applications in Basic Science and Rational Drug Design," *Bio/Technology*, 10:773–778 (1992).

Songyang, Z., et al., "SH2 Domains Recognize Specific Phosphopeptide Sequences," *Cell*, 72:767–778 (1993).

Burke Jr., T.R., et al., "Nonhydrolyzable Phosphotyrosyl Mimetics for the Preparation of Phosphatase–Resistant SH2 Domain Inhibitors," *Biochemistry*, 33:6490–6494 (1994).

Knappik, A. and Plückthun, A., "Engineered Turns of a Recombinant Antibody Improve its In Vivo Folding," *Protein Engineering*, 8(1):81–89 (1995).

Maraganore, J.M., "Design and Characterization of Hirulogs: A Novel Class of Bivalent Peptide Inhibitors of Thrombin," *Biochemistry*, 29:7095–7101 (1990).

Keane, A.M., et al., "Peptide Mimetics of an Actin–Binding Site on Myosin Span Two Functional domains on Actin," *Nature*, 344:265–268 (1990).

Wells, J.A., "Hormone Mimicry," *Science*, 273:449–450 (1996).

Livnah, O., et al., "Functional Mimicry of a Protein Hormone by a Peptide Agonist: The EPO Receptor Complex at 2.8 Å," *Science*, 273:464–471 (1996)

Wrighton, N.C., "Small Peptides as Potent Mimetics of the Protein Hormone Erythropoietin," *Science*, 273:458–463 (1996).

Saragovi, H.U., et al., "Design and Synthesis of a Mimetic From an Antibody Complementarity–Determining Region," *Science*, 253:792–795 (1991).

Baily, E,. et al., "Phosphorylation of Two Small GTP–Binding Proteins of the Rab Family by $p34^{cdc2}$," *Nature*, 350:715–718 (1991).

Lu, K.P., et al., "Evidence for a NIMA–Like Mitotic Pathway in Vertebrate Cells," *Cell*, 81:413–424 (1995).

Ranganathan, R., et al., "Structural and Functional Analysis of the Mitotic Rotamase Pin1 Suggests Substrate Recognition is Phosphorylation Dependent," *Cell*, 89:875–886 (1997).

Lu, K.P., et al., "A Human Peptidyl–Prolyl Isomerase Essential for Regulation of Mitosis," *Nature*, 380:544–547 (1996).

Johnson, T., et al., "Backbone protection and its application to the synthesis of a difficult phosphopeptide sequence," *Journal of the Chemical Society*, No. 7:719–728 (Apr. 7, 1996).

Welsh, G.I., et al., "Peptide substrates suitable for assaying glycogen synthase kinase–3 in crude cell extracts," *Analytical Biochemistry*, 244:16–21 (1997).

Tsukamoto, M., et al., "Improved protective groups for phosphate of O–phosphoserine useful for the solid–phase peptide synthesis," *Tetrahedron Letters*, 32 No. 48:7083–7086 (Nov. 25, 1991).

Shapiro, G., et al., "FMOC solid phase synthesis of serine phosphopeptides via selective protection of serine and on resin phosphorylation," *Tetrahedron Letters*, 35 No. 6:869–872 (Feb. 7, 1994).

Hodges, R.A., et al., "Peptides, structure, chemistry and Biology," Escom, Leiden, The Netherlands, 799–801 (1994).

Resing, R.A., et al., "Mass spectrometric analysis fo 21 phosphorylation sites in the internal repeat of rat profilaggrin, precursor of an intermediate filament association protein," *Biochemistry*, 34 No. 29:9477–9487 (Jul. 25, 1995).

Lang, E., et al., "Spectroscopic evidence that monoclonal antibodies recognize the domainant conormation of medium–sized sinthetic peptides," *Journal of Immunological Methods*, 170 No. 1: 103–115 (1994).

Fiol, C.J., et al., "Ordered multisite protein phosphorylation," *Journal of Biological Chemistry*, 265 No. 11: 6061–6065 (Apr. 15, 1990).

Otvos, Jr., L., et al., "Solid–phase synthesis of peptides," *International Journal of Peptide and Protein Research,* 34 No. 2:129–133 (Jul. 1989).

Yaffe, M.B., et al., "The structural basis for 14–3–3: phosphopeptide binding specificity," *Cell,* 91 No. 7:961–971 (Dec. 26, 1997).

Yaffe, M.B., et al., "Sequence–Specific and phosphorylation–dependent proline isomerization; a potential mitotic regulation mechanism," *Science,* 278:1957–1960 (Dec. 12, 1997).

Burnhardt, A., et al., "The Solid–Phase Synthesis of Side–Chain–Phosphorylate Peptide–4–Nitroanilides," *J. Peptide Res., 50:*143–152 (1997).

* cited by examiner

SEQUENCE LISTING

<160> NUMBER OF SEQ ID NOS: 54

<210> SEQ ID NO 1
<211> LENGTH: 8
<212> TYPE: PRT
<213> ORGANISM: synthetic nucleotide
<220> FEATURE:
<221> NAME/KEY: PHOSPHORYLATION
<222> LOCATION: (4)...(5)
<221> NAME/KEY: VARIANT
<222> LOCATION: (1)...(8)
<223> OTHER INFORMATION: Xaa = Any Amino Acid

<400> SEQUENCE: 1

Xaa Xaa Xaa Ser Pro Xaa Xaa Xaa
1               5

<210> SEQ ID NO 2
<211> LENGTH: 12
<212> TYPE: PRT
<213> ORGANISM: synthetic nucleotide
<220> FEATURE:
<221> NAME/KEY: PHOSPHORYLATION
<222> LOCATION: (6)...(6)
<221> NAME/KEY: VARIANT
<222> LOCATION: (1)...(12)
<223> OTHER INFORMATION: Xaa = Any Amino Acid

<400> SEQUENCE: 2

Met Ala Xaa Xaa Xaa Ser Xaa Xaa Xaa Ala Lys Lys
1               5                   10

<210> SEQ ID NO 3

```
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 3

Ala Ala Pro Leu Asn Ala
 1               5

<210> SEQ ID NO 4
<211> LENGTH: 7
<212> TYPE: PRT
<213> ORGANISM: synthetic nucleotide
<220> FEATURE:
<221> NAME/KEY: PHOSPHORYLATION
<222> LOCATION: (6)...(6)

<400> SEQUENCE: 4

Ala Ala Ala Pro Arg Asn Ala
 1               5

<210> SEQ ID NO 5
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 5

Ala Ala Pro Met Asn Ala
 1               5

<210> SEQ ID NO 6
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 6

Ala Asp Pro Tyr Asn Ala
 1               5

<210> SEQ ID NO 7
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 7

Ala Glu Pro Phe Asn Ala
 1               5

<210> SEQ ID NO 8
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 8
```

Ala Tyr Pro Tyr Asn Ala
1               5

<210> SEQ ID NO 9
<211> LENGTH: 6
<212> TYPE: PRT
<213> ORGANISM: synthetic nucleotide
<220> FEATURE:
<221> NAME/KEY: PHOSPHORYLATION
<222> LOCATION: (2)...(2)
<221> NAME/KEY: PHOSPHORYLATION
<222> LOCATION: (5)...(5)

<400> SEQUENCE: 9

Ala Tyr Pro Tyr Asn Ala
1               5

<210> SEQ ID NO 10
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 10

Ala Ser Pro Tyr Asn Ala
1               5

<210> SEQ ID NO 11
<211> LENGTH: 6
<212> TYPE: PRT
<213> ORGANISM: synthetic nucleotide
<220> FEATURE:
<221> NAME/KEY: PHOSPHORYLATION
<222> LOCATION: (2)...(2)
<221> NAME/KEY: PHOSPHORYLATION
<222> LOCATION: (5)...(5)

<400> SEQUENCE: 11

Ala Ser Pro Tyr Asn Ala
1               5

<210> SEQ ID NO 12
<211> LENGTH: 6
<212> TYPE: PRT
<213> ORGANISM: synthetic nucleotide
<220> FEATURE:
<221> NAME/KEY: PHOSPHORYLATION
<222> LOCATION: (5)...(5)

<400> SEQUENCE: 12

Ala Thr Pro Tyr Asn Ala
1               5

<210> SEQ ID NO 13
<211> LENGTH: 6
<212> TYPE: PRT
<213> ORGANISM: synthetic nucleotide
<220> FEATURE:
<221> NAME/KEY: PHOSPHORYLATION
<222> LOCATION: (2)...(2)
<221> NAME/KEY: PHOSPHORYLATION
<222> LOCATION: (5)...(5)

<400> SEQUENCE: 13

Ala Thr Pro Tyr Asn Ala
1               5

```
<210> SEQ ID NO 14
<211> LENGTH: 7
<212> TYPE: PRT
<213> ORGANISM: synthetic nucleotide
<220> FEATURE:
<221> NAME/KEY: PHOSPHORYLATION
<222> LOCATION: (6)...(6)

<400> SEQUENCE: 14

Ala Ala Glu Pro Phe Asn Ala
 1               5

<210> SEQ ID NO 15
<211> LENGTH: 7
<212> TYPE: PRT
<213> ORGANISM: synthetic nucleotide
<220> FEATURE:
<221> NAME/KEY: PHOSPHORYLATION
<222> LOCATION: (6)...(6)

<400> SEQUENCE: 15

Ala Ala Ser Pro Phe Asn Ala
 1               5

<210> SEQ ID NO 16
<211> LENGTH: 7
<212> TYPE: PRT
<213> ORGANISM: synthetic nucleotide
<220> FEATURE:
<221> NAME/KEY: PHOSPHORYLATION
<222> LOCATION: (3)...(3)
<221> NAME/KEY: PHOSPHORYLATION
<222> LOCATION: (6)...(6)

<400> SEQUENCE: 16

Ala Ala Ser Pro Phe Asn Ala
 1               5

<210> SEQ ID NO 17
<211> LENGTH: 7
<212> TYPE: PRT
<213> ORGANISM: synthetic nucleotide
<220> FEATURE:
<221> NAME/KEY: PHOSPHORYLATION
<222> LOCATION: (6)...(6)

<400> SEQUENCE: 17

Ala Ala Thr Pro Phe Asn Ala
 1               5

<210> SEQ ID NO 18
<211> LENGTH: 7
<212> TYPE: PRT
<213> ORGANISM: synthetic nucleotide
<220> FEATURE:
<221> NAME/KEY: PHOSPHORYLATION
<222> LOCATION: (3)...(3)
<221> NAME/KEY: PHOSPHORYLATION
<222> LOCATION: (6)...(6)

<400> SEQUENCE: 18

Ala Ala Thr Pro Phe Asn Ala
 1               5

<210> SEQ ID NO 19
<211> LENGTH: 7
<212> TYPE: PRT
<213> ORGANISM: synthetic nucleotide
```

```
<220> FEATURE:
<221> NAME/KEY: PHOSPHORYLATION
<222> LOCATION: (6)...(6)

<400> SEQUENCE: 19

Ala Ala Ser Pro Arg Asn Ala
1               5

<210> SEQ ID NO 20
<211> LENGTH: 7
<212> TYPE: PRT
<213> ORGANISM: synthetic nucleotide
<220> FEATURE:
<221> NAME/KEY: PHOSPHORYLATION
<222> LOCATION: (3)...(3)
<221> NAME/KEY: PHOSPHORYLATION
<222> LOCATION: (6)...(6)

<400> SEQUENCE: 20

Ala Ala Ser Pro Arg Asn Ala
1               5

<210> SEQ ID NO 21
<211> LENGTH: 8
<212> TYPE: PRT
<213> ORGANISM: synthetic nucleotide
<220> FEATURE:
<221> NAME/KEY: PHOSPHORYLATION
<222> LOCATION: (3)...(3)
<221> NAME/KEY: PHOSPHORYLATION
<222> LOCATION: (7)...(7)

<400> SEQUENCE: 21

Trp Tyr Ser Pro Arg Thr Asn Ala
1               5

<210> SEQ ID NO 22
<211> LENGTH: 7
<212> TYPE: PRT
<213> ORGANISM: synthetic nucleotide
<220> FEATURE:
<221> NAME/KEY: PHOSPHORYLATION
<222> LOCATION: (3)...(3)
<221> NAME/KEY: PHOSPHORYLATION
<222> LOCATION: (6)...(6)

<400> SEQUENCE: 22

Ala Ala Thr Pro Arg Asn Ala
1               5

<210> SEQ ID NO 23
<211> LENGTH: 8
<212> TYPE: PRT
<213> ORGANISM: synthetic nucleotide
<220> FEATURE:
<221> NAME/KEY: PHOSPHORYLATION
<222> LOCATION: (7)...(7)

<400> SEQUENCE: 23

Trp Phe Tyr Ser Pro Arg Asn Ala
1               5

<210> SEQ ID NO 24
<211> LENGTH: 8
<212> TYPE: PRT
<213> ORGANISM: synthetic nucleotide
<220> FEATURE:
<221> NAME/KEY: PHOSPHORYLATION
<222> LOCATION: (4)...(4)
```

```
<221> NAME/KEY: PHOSPHORYLATION
<222> LOCATION: (7)...(7)

<400> SEQUENCE: 24

Trp Phe Tyr Ser Pro Arg Asn Ala
1               5

<210> SEQ ID NO 25
<211> LENGTH: 8
<212> TYPE: PRT
<213> ORGANISM: synthetic nucleotide
<220> FEATURE:
<221> NAME/KEY: PHOSPHORYLATION
<222> LOCATION: (4)...(4)
<221> NAME/KEY: PHOSPHORYLATION
<222> LOCATION: (7)...(7)

<400> SEQUENCE: 25

Trp Phe Tyr Ser Pro Arg Asn Ala
1               5

<210> SEQ ID NO 26
<211> LENGTH: 6
<212> TYPE: PRT
<213> ORGANISM: synthetic nucleotide
<220> FEATURE:
<221> NAME/KEY: PHOSPHORYLATION
<222> LOCATION: (4)...(4)

<400> SEQUENCE: 26

Trp Phe Tyr Ser Pro Arg
1               5

<210> SEQ ID NO 27
<211> LENGTH: 8
<212> TYPE: PRT
<213> ORGANISM: synthetic nucleotide

<400> SEQUENCE: 27

Tyr Val Gly Thr Pro Phe Tyr Met
1               5

<210> SEQ ID NO 28
<211> LENGTH: 8
<212> TYPE: PRT
<213> ORGANISM: synthetic nucleotide

<400> SEQUENCE: 28

Phe Tyr Met Ser Pro Glu Ile Cys
1               5

<210> SEQ ID NO 29
<211> LENGTH: 8
<212> TYPE: PRT
<213> ORGANISM: synthetic nucleotide

<400> SEQUENCE: 29

Ile Leu Asn Thr Pro Val Ile Arg
1               5

<210> SEQ ID NO 30
<211> LENGTH: 8
<212> TYPE: PRT
<213> ORGANISM: synthetic nucleotide

<400> SEQUENCE: 30
```

```
Glu Ser Arg Thr Pro Phe Thr Arg
 1               5
```

<210> SEQ ID NO 31
<211> LENGTH: 8
<212> TYPE: PRT
<213> ORGANISM: synthetic nucleotide

<400> SEQUENCE: 31

```
Lys Ser Arg Ser Pro His Arg Arg
 1               5
```

<210> SEQ ID NO 32
<211> LENGTH: 8
<212> TYPE: PRT
<213> ORGANISM: synthetic nucleotide

<400> SEQUENCE: 32

```
Glu Met Pro Ser Pro Phe Leu Ala
 1               5
```

<210> SEQ ID NO 33
<211> LENGTH: 8
<212> TYPE: PRT
<213> ORGANISM: synthetic nucleotide

<400> SEQUENCE: 33

```
Tyr Leu Gly Ser Pro Ile Thr Thr
 1               5
```

<210> SEQ ID NO 34
<211> LENGTH: 8
<212> TYPE: PRT
<213> ORGANISM: synthetic nucleotide

<400> SEQUENCE: 34

```
Ala Asn Ile Thr Pro Arg Glu Gly
 1               5
```

<210> SEQ ID NO 35
<211> LENGTH: 8
<212> TYPE: PRT
<213> ORGANISM: synthetic nucleotide

<400> SEQUENCE: 35

```
Gly Arg Arg Ser Pro Arg Pro Asp
 1               5
```

<210> SEQ ID NO 36
<211> LENGTH: 8
<212> TYPE: PRT
<213> ORGANISM: synthetic nucleotide

<400> SEQUENCE: 36

```
Phe Leu Trp Ser Pro Phe Glu Ser
 1               5
```

<210> SEQ ID NO 37
<211> LENGTH: 8
<212> TYPE: PRT
<213> ORGANISM: synthetic nucleotide

<400> SEQUENCE: 37

```
Ala Ser Cys Ser Pro Ile Ile Met
 1               5
```

<210> SEQ ID NO 38
<211> LENGTH: 8
<212> TYPE: PRT
<213> ORGANISM: synthetic nucleotide

<400> SEQUENCE: 38

Leu Arg Lys Ser Pro Phe Cys Arg
1               5

<210> SEQ ID NO 39
<211> LENGTH: 8
<212> TYPE: PRT
<213> ORGANISM: synthetic nucleotide

<400> SEQUENCE: 39

Tyr Phe Ile Ser Pro Phe Gly His
1               5

<210> SEQ ID NO 40
<211> LENGTH: 8
<212> TYPE: PRT
<213> ORGANISM: synthetic nucleotide

<400> SEQUENCE: 40

Arg Ser Arg Ser Pro Arg Arg Arg
1               5

<210> SEQ ID NO 41
<211> LENGTH: 8
<212> TYPE: PRT
<213> ORGANISM: synthetic nucleotide

<400> SEQUENCE: 41

Asp Ser Ala Ser Pro Arg Tyr Ile
1               5

<210> SEQ ID NO 42
<211> LENGTH: 8
<212> TYPE: PRT
<213> ORGANISM: synthetic nucleotide

<400> SEQUENCE: 42

Phe Phe Arg Ser Pro Arg Arg Met
1               5

<210> SEQ ID NO 43
<211> LENGTH: 8
<212> TYPE: PRT
<213> ORGANISM: synthetic nucleotide

<400> SEQUENCE: 43

Asp Pro Tyr Ser Pro Arg Ile Gln
1               5

<210> SEQ ID NO 44
<211> LENGTH: 8
<212> TYPE: PRT
<213> ORGANISM: synthetic nucleotide

<400> SEQUENCE: 44

Phe Gly Phe Ser Pro Ser Gly Thr
1               5

```
<210> SEQ ID NO 45
<211> LENGTH: 8
<212> TYPE: PRT
<213> ORGANISM: synthetic nucleotide

<400> SEQUENCE: 45

Gln Leu Arg Ser Pro Arg Arg Thr
 1               5

<210> SEQ ID NO 46
<211> LENGTH: 8
<212> TYPE: PRT
<213> ORGANISM: synthetic nucleotide

<400> SEQUENCE: 46

Tyr Gly Lys Ser Pro Tyr Leu Tyr
 1               5

<210> SEQ ID NO 47
<211> LENGTH: 8
<212> TYPE: PRT
<213> ORGANISM: synthetic nucleotide

<400> SEQUENCE: 47

Lys Ile Arg Ser Pro Arg Arg Phe
 1               5

<210> SEQ ID NO 48
<211> LENGTH: 8
<212> TYPE: PRT
<213> ORGANISM: synthetic nucleotide

<400> SEQUENCE: 48

Pro Cys Tyr Thr Pro Tyr Tyr Val
 1               5

<210> SEQ ID NO 49
<211> LENGTH: 8
<212> TYPE: PRT
<213> ORGANISM: synthetic nucleotide

<400> SEQUENCE: 49

Gly Phe Phe Thr Pro Arg Leu Ile
 1               5

<210> SEQ ID NO 50
<211> LENGTH: 8
<212> TYPE: PRT
<213> ORGANISM: synthetic nucleotide

<400> SEQUENCE: 50

Trp Tyr Arg Ser Pro Arg Leu Leu
 1               5

<210> SEQ ID NO 51
<211> LENGTH: 8
<212> TYPE: PRT
<213> ORGANISM: synthetic nucleotide

<400> SEQUENCE: 51

Phe Met Met Thr Pro Tyr Val Val
 1               5

<210> SEQ ID NO 52
<211> LENGTH: 8
```

```
-continued

<212> TYPE: PRT
<213> ORGANISM: synthetic nucleotide

<400> SEQUENCE: 52

Trp Gly Ile Ser Pro Arg Gly Ala
 1               5

<210> SEQ ID NO 53
<211> LENGTH: 8
<212> TYPE: PRT
<213> ORGANISM: synthetic nucleotide

<400> SEQUENCE: 53

Asn Trp Arg Ser Pro Arg Leu Arg
 1               5

<210> SEQ ID NO 54
<211> LENGTH: 7
<212> TYPE: PRT
<213> ORGANISM: synthetic nucleotide
<220> FEATURE:
<221> NAME/KEY: VARIANT
<222> LOCATION: (1)...(7)
<223> OTHER INFORMATION: Xaa = Any Amino Acid

<400> SEQUENCE: 54

Xaa Xaa Ser Thr Xaa Xaa Xaa
 1               5
```

INHIBITORS OF PHOSPHOSERINE AND PHOSPHOTHREONINE-PROLINE-SPECIFIC ISOMERASES

RELATED APPLICATION

This application claims priority provisional application Serial No.: 60/058,164 filed Apr. 8, 1997, the entire teachings of which are incorporated herein by reference.

GOVERNMENT FUNDING

This invention was made with U.S. Government support under USPHS Grant Nos. RO1 GM56230 and GM56203. The United States government has certain rights in the invention.

BACKGROUND

Events of the eukaryotic cell cycle are regulated by an evolutionarily conserved set of protein kinases. The cyclin-dependent kinases (Cdks) are important for driving cells through different phases of the cell cycle and their sequential activation and inactivation are tightly regulated. At the G2/M transition, activation of the mitotic Cdk, Cdc2, requires multiple events; these include the synthesis and binding of cyclin B, phosphorylation on Cdc2 at an activating site by Cak, and finally, Cdc25-dependent dephosphorylation of inactivating sites that have been phosphorylated by Wee1 and Myt1 (P. Nurse, *Cell* 79:547 (1994); R. W. King, P. K. Jackson, M. W. Kirschner, *Cell* 79:563 (1994); T. R. Coleman, W. G. Dunphy, *Curr. Opin. Cell Biol.* 6:877 (1994)).

How activation of a Cdk elicits the downstream events of cell cycle progression is less well understood. Activation of cyclin B/Cdc2 leads to the phosphorylation of a large number of proteins, mainly on sites containing a Ser/Thr-Pro motif. Protein phosphorylation is believed to alter the functions of proteins to trigger the events of mitosis. In a few cases, mitotic phosphorylation has been shown to regulate mitotic events (R. Heald and F. McKeon, *Cell* 61:579 (1990); E. Bailly, et al., *Nature* 350:715 (1991); A. Blangy, et al., *Cell* 83:1159 (1995)). However, it is not understood how the rapid changes in mitotic phosphorylation are converted to the sequential events of mitosis.

An important experimental tool which has uncovered the general role of phosphorylation in mitotic regulation is the MPM-2 monoclonal antibody (F. M. Davis, et al., *Proc. Natl. Acad. Sci. USA* 80:2926 (1983)). MPM-2 recognizes a Phospho.Ser/Thr-Pro epitope on approximately 50 proteins which are localized to various mitotic structures (J. M. Westendorf, P. N. Rao, L. Gerace, *Proc. Natl. Acad. Sci. USA* 91:714–8 (1994)). Several important mitotic regulators are recognized by this antibody, including Cdc25, Wee1, topoisomerase IIa, Cdc27, Map 4, INCENP and NIMA (Stukenberg, P. T., K. D. Lustig, T. J. McGarry, R. W. King, J. Kuang and M. W. Kirschner, *Curr Biol* 7:338–348 (1997)).

Currently six kinases have been shown to phosphorylate proteins in vitro to produce the MPM-2 epitope: Cdc2, Polo-like kinase (Plk1), NIMA, MAP kinase, a MAP kinase (MEK), and an unidentified activity ME-H (Kuang, J. and C. L. Ashorn., *J Cell Biol* 123:859–868 (1993); Taagepera et al., *Mol Biol Cell* 5:1243–1251 (1994); Kumagai, A. and W. G. Dunphy, *Science* 273:1377–1380 (1996); Renzi, L., M. S. Gersch, M. S. Campbell, L. Wu, S. A. Osmani and G. J. Gorbsky, *J. Cell Sci* 110:2013–2025 (1997)). However, these kinases also phosphorylate substrates that do not generate the MPM-2 epitope especially in cell cycle stages other than mitosis. This suggests that there are additional features that are required for the recognition by MPM-2. Determination of the optimal MPM-2 binding sequence have confirmed the importance of amino acid residues flanking the Phospho Ser/Thr-Pro motif for the MPM-2 recognition (Westendorf, J. M., P. N. Rao and L. Gerace. *Proc Natl Acad Sci USA* 91:714–718 (1994)). Westendorf, et al., 1994).

SUMMARY OF THE INVENTION

The present invention is based on the discovery that an essential mitotic peptidyl prolyl isomerase specifically recognizes phosphorylated serine/threonine-proline bonds present in mitotic phosphoproteins. As a result of this discovery, a novel class of moleculular compounds are available with activity to act as inhibitors of phosphoserine/phosphothreonine-proline specific peptidyl prolyl isomerases, in particular the peptidyl prolyl isomerase, Pin1, and other Pin1-like isomerases. Accordingly, these molecular inhibitors are useful to treat disorders of cell proliferation such as hyperplastic or neoplastic disorders, wherein treatment of the disorder with an inhibitor of the present invention results in the arrest of mitosis and apoptosis (cell death) of the target cells.

The inhibitor compounds of the present invention include any molecule that binds into the active site of the phosphoserine- or phosphothreonine-proline specific peptidyl prolyl isomerase and, upon binding to the isomerase, inhibits the isomerase activity. Encompassed by the present invention are inhibitor compounds that mimic the structure and conformation of the substrate moiety when bound to the catalytic site (also referred to herein as the active site) of the isomerase. Molecular inhibitors of the the present invention will typically have an inhibition constant ($K_i$) in the nanomolar to micromolar range. Specifically encompassed herein are organic molecules that mimic the structure and conformation of pSer/pThr and bind to the isomerase of interest, thereby inhibiting its activity.

The inhibitor compounds of the present invention inculde inhibitors that comprise a core region that mimics the pSer/pThr-Pro peptide moiety of the phosphoserine- or phosphothreonine-proline peptidyl prolyl isomerase substrate. Encompassed by the present invention are inhibitors that comprise the pSer/pThr mimic moiety with the mimic moiety being flanked on one side by hydrophobic groups and on the other side by hydrophobic or positively charged groups, wherein the groups would contact the active site of the isomerase of interest.

The inhibitor compounds of the present invention include compounds that contain a core sequence comprising xSer/xThrY wherein "x" is a negatively charged tetra- or pentavalent moiety and "Y" is a Pro (proline) or a Pro analog. More specifically, the inhibitors of the present invention include compounds that inhibit a phosphoserine- or phosphothreonine-proline specific peptidyl-prolyl isomerase comprising a protein, polypeptide, peptide and/or a peptide mimetic wherein said protein, polypeptide, peptide or peptide mimetic comprises pSer/pThr. Specifically encompassed are inhibitors that have the core sequence of XXXpSer-pProXXX (SEQ ID NO.:1), wherein X is any L-amino acid or D-amino acid.

Candidate molecules of the present invention are evaluated for inhibitory activity in competitive inhibition assays. For example, the assay mixture would include the candidate molecule to be tested for inhibiting activity, the isomerase of interest and the intended substrate of the isomerase of interest. This admixture is maintained for a time sufficient and under conditions sufficient for the isomerase of interest to bind and catalyze the isomerization of its intended substrate. The catalytic activity of the isomerase of interest in the presence of the candidate inhibitor is then compared with the activity of the isomerase in the absence of the candidate inhibitor. If the activity of the isomerase in the presence of the inhibitor is less than the activity of the isomerase in the absence of the inhibitor, the candidate inhibitor is suitable for use as an inhibitor of the isomerase of interest.

Encompassed by the present invention are inhibitors of interphase-specific pSer/pThr-Pro specific peptidyl prolyl isomerases. Specifically encompassed by the present invention are inhibitors of the essential mitotic peptidyl prolyl isomerase, Pin1, and other PIN1-like isomerases.

Also encompassed by the present invention are methods of inhibiting mitotic peptidyl-prolyl isomerases comprising administering an effective amount of an inhibitor as described herein. For example, a composition comprising an effective amount of the inhibitor and a pharmaceutically acceptable carrier can be administered to an individual in need thereof. Specifically encompassed are methods of inhibiting unwanted cell growth resulting from a hyperplastic or neoplastic disorder. Also encompassed by the present invention are methods of inhibiting cell growth in target cells, comprising contacting the cells with an inhibitor as described herein.

The present invention also relates to libraries of peptides that comprises a mixture of substantially equimolar amounts of peptides comprising the sequence $NH_2$-MAXXXpSXXXAKK (SEQ ID NO.:2), wherein for each peptide X is any amino acid.

The present invention also relates to methods of identifying a phosphorserine-or phosphothreonine-specific peptidyl prolyl isomerase inhibitor comprising the steps of:
  a) providing a library of compounds that comprises a mixture of substantially equimolar amounts of peptides comprising the sequence $X_1X_2X_3pS$-$PX_4X_5X_6$, wherein for each peptide X is any amino acid;
  b) contacting the library of a) with the peptidyl prolyl isomerase of interest under binding conditions for time sufficient for the isomerase to bind to the peptides;
  c) determining the amino acid sequences of peptides bound to the isomerase of interest;
  d) synthesizing the peptides of c); and
  e) assaying peptides of d) for cis/trans isomerization by the peptidyl prolyl isomerase of interest to determine which peptides undergo isomerization by the isomerase of interest, thus identifying peptides that bind to the isomerase and are suitable for use as inhibitors of the isomerase of interest.

The present invention further relates to methods of identifying a phosphorserine or phosphothreonine-specific peptidyl prolyl isomerase inhibitor comprising the steps of:
  a) providing the peptidyl prolyl isomerase of interest;
  b) mixing the isomerase of interest with:
    i) a candidate molecule and
    ii) the substrate of the isomerase of interest to form an admixture of the isomerase of interest, candidate molecule and substrate;
  c) maintaining the admixture of b) under conditions sufficient for the isomerase of interest to catalyze the cis/trans isomerization of the substrate; and
  d) determining the $K_i$ of the candidate molecule, wherein a $K_i$ of 10 micromolar or less is indicative of an inhibitor of the peptidyl prolyl isomerase of interest.

DETAILED DESCRIPTION OF THE INVENTION

Figure 1:
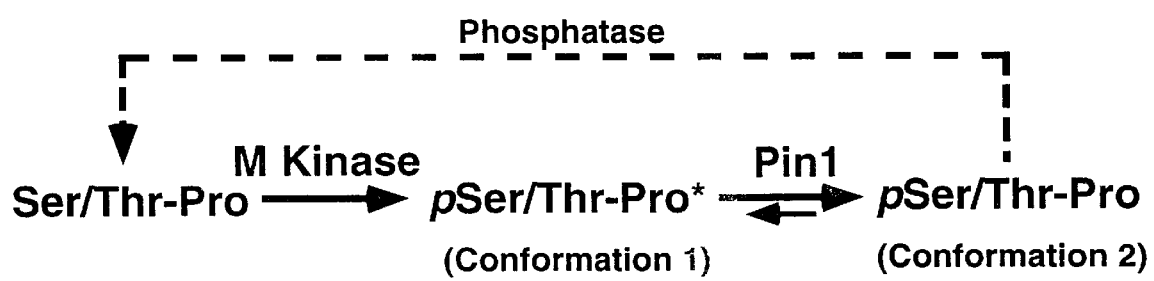
FIG. 1 depicts a model for the Pin1-dependent regulation of mitosis-specific phosphoproteins that are phosphorylated by Cdc2 and other mitotic kinases (M kinase).

The present invention is related to the discovery that an essential mitotic pepidyl-prolyl isomerase (PPIase) recognizes phosphorylated serine/threonine (pSer/pThr) bonds present in mitotic phosphoproteins. Pin1 is an essential peptidyl-prolyl cis-trans isomerase (PPIase). It is distinct from two other well-characterized PPIase families: the cyclophilins and the FK-506-binding proteins (FKBPs), which are targets for the immunosuppressive drugs cyclosporin A and FK506, respectively (reviewed in Schreiber, S. L., *Science* 251:283–287 (1991)).

PPIases are ubiquitous enzymes that catalyze rotation about the peptide bond preceding a Pro residue, and may accelerate the folding and trafficking of some proteins (reviewed in Schmid, F. X., *Curr. Biol.* 5:993–994 (1995)). Interestingly, inhibition of PPIase activity is not required for the immunosuppressive property of cyclosporin A and FK506. Furthermore, neither the cyclophilins nor the FKBPs are essential for normal cell growth. Thus, evidence for the biological importance of PPIase enzymatic activity has been limited.

In contrast, Pin1 contains a PPIase domain that is essential for cell cycle progression and its subcellular localization is tightly regulated at the G2/M transition (Lu, K. P., S. D. Hanes and T. Hunter, *Nature* 380:544–547 (1996)). Pin1 is localized in a defined nuclear substructure in interphase, but is concentrated to the condensed chromatin, with some staining in other structures, during mitosis. Furthermore, depletion of Pin1 protein in HeLa cells or Pin1/Ess1p in yeast results in mitotic arrest, whereas overexpression of Pin1 induces a G2 arrest. These results suggest that Pin1 is an essential mitotic regulator that both negatively regulates entry into mitosis and is required for progression through mitosis.

As described herein, Pin1-binding proteins have been identified in human cells and Xenopus extracts. Pin1 has been identified in all eukaryotic organisms where examined, including plants, yeast, Aspergillus, and mammals (sequences deposited in GenBank). Results indicate that although Pin1 levels are constant throughout the cell cycle, the interaction of Pin1 and its targets is cell cycle-regulated and depends upon mitotic phosphorylation of target proteins.

Pin1 directly interacts with a large subset of mitosis-specific phosphoproteins, which includes Cdc25, Wee1, Myt1, Plk1, Cdc27 and E-MAP115 as well as some others recently identified by a screen for mitotic phosphoproteins (Stukenberg, P. T., K. D. Lustig, T. J. McGarry, R. W. King, J. Kuang and M. W. Kirschne, *Curr Biol* 7:338–348 (1997)). Many of these Pin1-interacting proteins are also recognized by the MPM-2 antibody. In functional assays, microinjection of Pin1 inhibits mitotic division in Xenopus embryos and entry into mitosis in Xenopus extracts, as is the case in HeLa and yeast cells. Furthermore, Pin1 binds the mitotically phosphorylated form of Cdc25 in vitro and in vivo, and it binds Cdc25 on the important phosphorylation sites and inhibits its activity. This characterization of the Pin1-Cdc25 interaction can at least partially explain the ability of Pin1 to inhibit the G2/M transition. All these activities of Pin1 are dependent upon the ability of Pin1 to mitotic phosphoproteins since the activities are disrupted by point mutations which inhibit the ability of Pin1 to recognize this unique class of phosphoproteins.

Also as described herein, Pin1 is a sequence-specific and phosphorylation-dependent PPIase that can specifically recognize the phosphorylated Ser/Thr-Pro bonds present in mitotic phosphoproteins. These results suggest that Pin1 acts as a general modulator of mitotic phosphoprotein activity, presumably by catalyzing phosphorylation-dependent Pro isomerization.

The crystal structure of human Pin1 complexed with an Ala-Pro dipeptide suggests that the isomerization mechanism of Pin1 includes general acid-base and covalent catalysis during peptide bond isomerization (Ranganathan et al., Cell 89:875–886 (1997)). More interestingly, Pin1 displays a unique substrate specificity. It prefers an acidic residue N-terminal to the isomerized Pro bond due to interaction of the acidic side chain with a basic cluster in Pin1. This basic cluster consists of the highly conserved residues Lys63, Arg68, and Arg69 at the entrance to the active site. In the crystal structure, this conserved triad sequestered a sulfate ion in close proximity to the β methyl group of the Ala residue in the bound Ala-Pro dipeptide. One candidate for this negatively charged residue is Phospho.Ser/Thr.

To investigate how Pin1 interacts with essential mitotic proteins, a glutathione S-transferase (GST) Pin1 fusion protein was used to screen oriented degenerate peptide libraries. The oriented peptide library approach (Z. Songyang et al. Cell 72:767 (1993) was used to screen for optimal peptides. All amino acids except Cys were incorporated at equimolar amounts in each degenerate position, yielding a total theoretical degeneracy for both libraries of $19^6=4.7\times 10^7$ distinct peptide sequences. Pin1-GST beads and MPM2 antibody bound to protein-G beads were incubated with the peptide library mixtures and washed extensively. Bound peptides were eluted with 30% acetic acid and sequenced. The crystal structure of Pin1 containing an Ala-Pro dipeptide substrate revealed a sulfate ion located 5 Å from the $C_\beta$ carbon of Ala (A), suggesting that phosphorylated Ser (pSer) might be preferred at this site (R. Ranganathan, K. P. Lu, T. Hunter, J. P. Noel, Cell 89:875 (1997)).

Next a ps-containing degenerate peptide library of general sequence $NH_2$-MAXXXpSXXXAKK, where X includes every amino acid except Cys, was prepared. GST-Pin1 protein preferentially bound a subset of peptides with Pro (P) immediately COOH-terminal to pSer.

To investigate whether peptides containing pS-P were preferred substrates for the isomerase activity of Pin1, oligopeptide substrates were synthesized and assayed for cis/trans isomerization by Pin1 and by members of the cyclophilin (Cyp18) and FKBP (FHBP12) families of PPIases. The chromogenic oligopeptides were synthesized (A. Bernhardt, M. Drewello, & M. Schutkowski, Int. J. Peptide Protein Res. 50:143 (1997) and confirmed by NMR. Standard peptides were purchased from Bachem. PPIase activity was assayed and the bimolecular rate constants $k_{cat}/K_m$ were calculated according to the equation $k_{cat}/K_m=(k_{obs}-k_u)/$[PPIase], where $k_u$ is the first-order rate constant for spontaneous cis/trans isomerization and $k_{obs}$, is the pseudo-first-order rate constant for cis/trans isomerization in the presence of PPIase, as described in G. Fischer, H. Bang, C. Mech, Biomed. Biochim. Acta 43:1101 (1984) and in J. L. Kofron et al. Biochemistry 30:6127 (1991). Affinity of Pin1 for peptides was measured as described in Schutkowski, M., Wöllner, S., & Fischer, G. Biochemistry 34:13016, (1995)). Neither Cyp18 nor FKBP12 effectively catalyzed isomerization of peptides with pS/pT-P moieties (Table 1). In contrast, either Y-P or pY-P bonds were good substrates for both enzymes. Thus phosphorylation on S/T-P, but not Y-P, renders the prolyl-peptidyl bond resistant to the catalytic action of conventional PPIases, and suggests the need for a different enzyme to catalyze this reaction. Table 1. Interaction between Pin1 and Selected Mitotic Phosphoproteins

| Phosphorproteins | Interphase | Mitotic |
|---|---|---|
| Cdc25* | − | +++ |
| Plk1* | − | +++ |
| Plx1 | − | +++ |
| Wee1 | + | ++ |
| Mos | + | ++ |
| Cdc27* | − | +++ |
| NIMA | − | +++ |
| Sox3 | − | +++ |
| Xbr-1b | − | +++ |
| MP75 (E-MAP-115) | − | +++ |
| MP110 (Cdc5) | − | +++ |
| MP68 | − | +++ |
| MP30 | − | ++ |
| MP105 | + | + |
| MP48 | − | − |
| Cyclin B* | − | − |

The binding between Pin1 and all selected mitotic phosphoproteins was assayed by incubating synthesized proteins with interphase and mitotic Xenopus extracts, followed by precipitation with GST-Pin1beads. The Pin1 interactions with those proteins indicated with * were also confirmed by GST-Pin1 pull-down assay from endogenous interphase and mitotic HeLa cell extracts. +, a week but above background interaction; ++, readily detectable interaction; +++, strong interaction.

In contrast to cyclophilins and FKBPs, Pin1 isomerase activity was highly specific for peptides with pS/pT-P bonds (Table 2). Pin1 displayed little isomerase activity for substrates containing S/T-P bonds. However, phosphorylation of these peptides on S or T residues increased the $k_{cat}/K_m$ values up to 300-fold.

TABLE 2

Sequence-specific and phosphorylation-dependent PPIase activity of Pin1

| Substrate | | PPIase Activity kcat/KM $(mM^{-1}s^{-1})$ |
|---|---|---|
| AAPL-pNA | (SEQ ID NO: 3) | 55 |
| AAAPR-pNA | (SEQ ID NO: 4) | 121 |
| AAPM-pNA | (SEQ ID NO: 5) | 134 |
| ADPY-pNA | (SEQ ID NO: 6) | 220 |
| AEPF-pNA | (SEQ ID NO: 7) | 3410 |
| AYPY-pNA | (SEQ ID NO: 8) | 5 |
| ApYPY-pNA | (SEQ ID NO: 9) | 3 |
| ASPY-pNA | (SEQ ID NO: 10) | 269 |
| ApSPY-pNA | (SEQ ID NO: 11) | 3370 |
| ATPY-pNA | (SEQ ID NO: 12) | 635 |
| ApTPY-pNA | (SEQ ID NO: 13) | 2480 |

TABLE 2-continued

Sequence-specific and phosphorylation-dependent
PPIase activity of Pin1

| Substrate | | PPIase Activity kcat/KM (mM$^{-1}$s$^{-1}$) |
|---|---|---|
| AAEPF-pNA | (SEQ ID NO: 14) | 220 |
| AASPF-pNA | (SEQ ID NO: 15) | 9 |
| AapSPF-pNA | (SEQ ID NO: 16) | 3760 |
| AATPF-pNA | (SEQ ID NO: 17) | 4 |
| AapTPF-pNA | (SEQ ID NO: 18) | 1370 |
| AASPR-pNA | (SEQ ID NO: 19) | 7 |
| AApSPR-pNA | (SEQ ID NO: 20) | 9300 |
| WypSPRT-pNA | (SEQ ID NO: 21) | 14100 |
| AapTPR-pNA | (SEQ ID NO: 22) | 3700 |
| WFYSPR-pNA | (SEQ ID NO: 23) | 170 |
| WFYpSPR-pNA | (SEQ ID NO: 24) | 20160 |

Assays were done as described in Table 1 except that trypsin was used instead of chymotrypsin as an isomer-specific protease when peptides with Pro-Arg-pNA were used as substrates.

Pin1 had low isomerization activity for peptides containing an Ala-Pro peptide bond, whereas incorporation of Glu (E) or Asp (D) immediately preceding P to mimic the ps, increased isomerization activity. Peptides containing a Y or pY preceding Pro were poor substrates for Pin1. This substrate specificity distinguishes Pin1 from the conventional PPIases in the cyclophilin and FKBP families.

To further define the sequence specificity of Pin1, a degenerate peptide library containing a fixed pS-P sequence flanked by 3 degenerate positions on each side was used. Pin1 selected Arg or aromatic residues at the −1 and +1 positions of the pS-P motif (Table 3). Aromatic amino acids were also selected at the −3, Phe/Ile at the −2, and Leu/Ile at the +2 position of pS-P. On this basis, several additional peptides were synthesized as Pin1 substrates, as described above. Peptides with Arg introduced at the P+1 position proved better substrates with specificity constants increased up to 1300 fold compared to their non-phosphorylated counterparts (Table 2). Placing aromatic residues NH$_2$-terminal to the pS-P position made these peptides even better substrates (Table 2). The best substrate identified thus far (Trp-Phe-Tyr-pSer-Pro-Arg-pNA) (SEQ ID NO.:25) is the optimal sequence selected from the peptide library (Table 2 and 3). The apparent K$_m$ of Pin1 towards this peptide was 10 µM.

TABLE 3

Binding specificity of Pin1 and MPM-2

| | −3 | −2 | −1 | 0 | +1 | +2 | +3 |
|---|---|---|---|---|---|---|---|
| Pin1 | W | F | Y | pS | P | R | L | X |
| | Y | I | R | | | F | I | |
| | F | | F | | | Y | | |
| | | | W | | | W | | |
| MPM-2 | Y | W | F | pS | P | L | X | X |
| | F | F | L | | | I | | |
| | W | | I | | | V | | |
| | | | | | | F | | |
| | | | | | | M | | |

GST-Pin1 and MPM-2 were incubated with the pS-P oriented degenerate peptide library NH$_2$-MAXXXpSXXXAKK, where X contains every amino acid except Cys. After an extensive wash, peptides bound with GST-Pin1 were eluted and sequenced. Amino acids with a significant selection at each degenerate position are shown.

As described herein, Pin1 binds a large subset of mitotic phosphoproteins also recognized by the monoclonal antibody MPM-2. Therefore, the sequence specificity for MPM-2 recognition was evaluated. When immobilized MPM-2 antibody was probed with a peptide library containing only a pS as the orienting residue, there was a strong selection for peptides with P at the pS+1 position. Using the pS-P degenerate peptide library, MPM-2 strongly selected peptides with aromatic and aliphatic amino acids at the −3, −1 and +1 positions relative to pS-P (Table 3). This MPM-2 binding motif is similar to the sequence motif selected by Pin1 (Table 3) and explains the observation that Pin1 specifically interacts with MPM-2 antigens.

To determine the structural basis for the Pin1 substrate specificity, molecular model-building was performed and tested by site-directed mutagenesis. A peptide (Trp-Phe-Tyr-pSer-Pro-Arg) (SEQ ID NO.:26) was modeled into the Pin1 structure (R. Ranganathan, K. P. Lu, T. Hunter, J. P. Noel, Cell 89:875 (1997) assuming that the phosphate group of pS occupies the position of of sulfate in the structure, The phosphate of pS in the modeled peptide was superimposed on the co-crystallizing SO$_4$ ion in the original Pin1 structure, and P residue displacements minimized with respect to the Ala-Pro ligand in the original Pin1 structure using molecular modeling programs GRASP (A. Nicholls, K. Sharp, B. Honig. Proteins 11:281 (1991), Molscript and Raster3d. In this model, R68 and R69 of Pin1 coordinate the pS phosphate, a hydrophobic groove accepts the preceding aromatic tripeptide, and the side chain of C113 and H59 coordinate the isomerizing pS-P peptide bond with ω=90°, stabilizing the transition state between cis and trans configuration. To test these predictions from the model, site-directed Pin1 mutants were generated and their PPIase activity assayed as described herein and in K. P. Lu, S. D. Hanes, T. Hunter, Nature 380:544 (1996); K. P. Lu and T. Hunter, Cell 81:413 (1995).

Substitution of both R68 and R69 by Ala reduced the k$_{cat}$/K$_m$ to 1/500 that of wild type Pin1 for the phosphorylated substrate. The catalytic activity of Pin1$^{R68,69A}$ was the same as wild-type Pin1 for the unphosphorylated peptide substrate. Thus, this cluster of basic residues appears to participate in coordinating the phosphate of pS/pT. Parvulin (J. U. Rahfeld, et al., FEBS Lett. 352:180 (1994);idid 343:65 (1994); K. E. Rudd, et al., TIBS 20:12 (1995), the prototype of the Pin1 family of PPIases has R68 and R69 replaced by Glu and failed to catalyze the isomerization of pS-P peptidyl bonds, though it was very effective in catalyzing the P isomerization of the unphosphorylated peptide. Replacement of the catalytic H59 residue of Pin1 with Ala dramatically decreased the PPIase activity for both phosphorylated and unphosphorylated peptides; however, the specificity for phosphorylated over unphosphorylated substrates was unchanged. For Pin1 the K$_{cat}$/K$_m$ for the phosphorylated versus unphosphorylated substrate is 19,400/7, which is approximately equal to the similar ratio of 1120/<1 for Pin1$^{H59A}$. Thus H59 appears to play an important role in catalyzing P isomerization and/or binding the substrate P residue.

On the basis of amino acid preferences deduced in the 6 positions surrounding the pS-P motif for optimal Pin1 binding, a weighted screening of the SWISS-PROT sequence database. Protein sequence database screening was performed with the program INDOVINATOR, using an entropy-based weighing technique to score for relative information content at each amino acid position flanking the pS/pT-P motif with the quantitative peptide library results, which are shown qualitatively in Table 3. This scan revealed within the top 5% of highest scores several potentially important mitotic phosphoprotein targets for Pin1. Many of these proteins are involved in regulation of the cell cycle, cytoskeletal/spindle structure, DNA replication, transcription or RNA processing (Table 4).

TABLE 4

| Cell Cycle Regulatory Proteins | Predicted Binding Site(s) | | Binding Confirmed |
|---|---|---|---|
| NIMA | YVGTPFYM | (SEQ ID NO.: 27) | Yes |
| | FYMSPEIC | (SEQ ID NO.: 28) | |
| | ILNTPVIR | (SEQ ID NO.: 29) | |
| | ESRTPFTR | (SEQ ID NO.: 30) | |
| | KSRSPHRR | (SEQ ID NO.: 31) | |
| | EMPSPFLA | (SEQ ID NO.: 32) | |
| Cdc25C | YLGSPITT | (SEQ ID NO.: 33) | Yes |
| Plk1 | ANITPREG | (SEQ ID NO.: 34) | Yes |
| Wee1 | GRRSPRPD | (SEQ ID NO.: 35) | Yes |
| Cdc27 | FLWSPFES | (SEQ ID NO.: 36) | Yes |
| Cytoskeletal/Spindle Proteins | | | |
| E-MAP-115 | ASCSPIIM | (SEQ ID NO.: 37) | Yes |
| Centromere protein A | LRKSPFCR | (SEQ ID NO.: 38) | |
| Nedd 5 | YFISPFGH | (SEQ ID NO.: 39) | |
| Nuclear/Splicing/Transcriptional Proteins | | | |
| Splicing factor SC35 | RSRSPRRR | (SEQ ID NO.: 40) | Yes |
| DNA topoisomerase II - alpha | DSASPRYI | (SEQ ID NO.: 41) | |
| Lim 1 homeobox Protein | FFRSPRRM | (SEQ ID NO.: 42) | |
| Laminin beta-1 | DPYSPRIQ | (SEQ ID NO.: 43) | |
| Nuclear pore complex Unp214 | FGFSPSGT | (SEQ ID NO.: 44) | |
| Guanine-Nucleotide-related Proteins | | | |
| Rab 4 | QLRSPRRT | (SEQ ID NO.: 45) | Yes |
| Rab GDP dissociation inhibitor | YGKSPYLY | (SEQ ID NO.: 46) | |
| Protein Kinases/Phosphatases | | | |
| S6 kinase | KIRSPRRF | (SEQ ID NO.: 47) | Yes |
| Mkk2 | PCYTPYYV | (SEQ ID NO.: 48) | |
| Abl2 | GFFTPRLI | (SEQ ID NO.: 49) | |
| Erk3 | WYRSPRLL | (SEQ ID NO.: 50) | |
| Jnk1,2 | FMMTP YVV | (SEQ ID NO.: 51) | |
| PP2A | WGISPRGA | (SEQ ID NO.: 52) | |
| Tyrosine phosphatase PTP-H1 | NWRSPRLR | (SEQ ID NO.: 53) | |

Predicted and/or Confirmed Pin1 Substrates
Based on the amino acid preferences value in each of the 6 positions surrounding the pS/pT-P motif for optimal Pin1 binding (Table 3), a weighted screening of the SWISS-PROT sequence database was undertaken. This is a partial list of selected proteins with the top scores; human sequences are used whenever possible. Interactions between Pin1 and some of the indentified proteins have been confirmed in vitro. Pin1 not only binds these two proteins, but also suppresses their funtions ¶, the inter-action between Pin1 and SC35 is inferred from their colocalization.

Several of these predicted proteins, such as Rab4, Cdc25 and NIMA, undergo mitosis-specific phosphorylation (R. Heald and F. McKeon, Cell 61:579 (1990); E. Bailly, et al., Nature 350:715 (1991); A. Blangy, et al., Cell 83:1159 (1995): J. Kuang, et al., Mol. Biol. Cell 5:135 (1994); X. S. Ye, et al., EMBO J. 14:986 (1995)). Cdc25 and NIMA also binds to Pin1 in a phosphorylation-dependent manner, as described herein. Other proteins identified in this search, however, had not been previously suspected of interacting with Pin1; therefore, a few were further investigated as example cases. Rab4 and ribosomal S6 kinases were found to interact with Pin1 specifically in mitotic, but not in interphase extracts. Thus, Pin1 binds a wide functional range of mitotic phosphoproteins.

Differences in isomerase activity of Pin1 and other PPIases result from different organization of the X-P binding pocket. In all PPIases, a hydrophobic pocket sequesters the aliphatic P side chain (S. L. Schreiber, Science 251:2881 (1991); G. Fischer, Angew. Chem. Intl. Ed. Engl. 33:1415 (1994); F. X. Schmid, Curr. Biol. 5:993 (1995)), hence the residues responsible for determining substrate preference must reside at the entrance to the P-binding pocket. In Pin1 and its homologues (K. P. Lu, S. D. Hanes, T. Hunter, Nature 380:544 (1996); K. P. Lu and T. Hunter, Cell 81:413 (1995), S. D. Hanes, et al., Yeast 5:55 (1989); R. Maleszka, et al., Proc. Natl. Acad. Sci. USA 93:447 (1996)), a cluster of basic residues coordinate the pS phosphate, and determine the specificity of this isomerase. Absence of a basic pocket in the cyclophilins, FKBPs, and other members of the parvulin families of PPIases may explain their failure to isomerize the pS/pT-P bonds.

The specificity of Pin1 rationalizes Pin1-binding proteins and also predicts a number of novel potential Pin1 substrates, some of which have been confirmed as in vitro Pin1 targets. Furthermore, Pin1 and MPM-2 bind similar sequences and proteins, and have similar phenotypes, indicating that the wide conservation of MPM-2 epitopes across various species (J. Kuang, et al., Mol. Biol. Cell 5:135 (1994); X. S. Ye, et al., EMBO J. 14:986 (1995), F. M. Davis, et al., Proc. Natl. Acad. Sci. USA 80:2926 (1983); J. M. Westendorf, P. N. Rao, L. Gerace, idid 91:714–8 (1994); S. Taagepera, et al., Mol. Biol. Cell 5:1243 (1994); A. Kumagai, W. G. Dunphy, Science 273:1377–80 (1996) can be explained by recognition of this epitope by a highly conserved mitotic regulator, Pin1.

Based on the determination of specific substrates for Pin1, as described herein, inhibitors of Pin1, Pin1-like isomerases and other phospho-Ser/Thr-specific PPIases can be produced. Thus, the present invention provides compounds that inhibit phosphoserine- and phosphothreonine-specific peptidyl-prolyl isomerases. Specifically encompassed by the present invention are peptidyl prolyl isomerases that recognize phosphorylated serine/threonine-proline bonds present in mitotic phosphoproteins.

The inhibitor compounds of the present invention include any molecule that binds into the active site of the phosphoserine- or phosphothreonine-proline specific peptidyl prolyl isomerase and, upon binding to the isomerase, inhibits the isomerase activity. Encompassed by the present invention are inhibitor compounds that mimic the structure and conformation of the substrate moiety when bound to the catalytic site (also referred to herein as the active site) of the isomerase. Molecular inhibitors of the the present invention will typically have an inhibition constant ($K_i$) of ten micromolar, or less. Specifically encompassed are organic molecules that mimic the structure and conformation of pSer/pThr and bind to the isomerase of interest, thereby inhibiting its activity. Such inhibitors are of a size and conformation so that it will bind into the active site of the isomerase of interest. Typically the inhibitors will have a three-dimensional conformation of about 12 angstroms wide, about 15 angstroms long and about 15 angstroms deep. However the inhibitor can be as large as about 19 angstroms wide, about 20 angstroms long and 15 angstroms deep.

The inhibitor compounds of the present invention inculde inhibitors that comprise a core region (or moiety) that mimics the pSer/pThr moiety of the phosphoserine- or phosphothreonine-proline peptidyl prolyl isomerase substrate. Encompassed by the present invention are inhibitors that comprise the pSer/pThr mimic moiety with the mimic moiety being flanked on one side by hydrophobic groups and the other side of the mimic moiety being flanked by hydrophobic or positively charged groups, wherein the groups would contact the active site of the isomerase of interest.

Specifically encompassed by the present invention are inhibitor compounds comprising proteins, polypeptides and peptides. The proteins, polypeptides and peptides of the present invention comprise naturally-occurring amino acids (e.g., L-amino acids), non-naturally amino acids (e.g., D-amino acids), and small molecules that biologically and biochemically mimic the inhibitor peptides, referred to herein as peptide analogs, derivatives or mimetics. (Saragovi, H. U., et al., Bio/Technology, 10:773–778 (1992)). The protein, polypeptide or peptide inhibitors of the present invention can be in linear or cyclic conformation.

Compounds that have PPIase inhibiting activity can be identified using oriented degenerate peptide libraries as described herein. For example, a library of xSer/Thr-X-containing peptides of a defined length can be screened for specific binding to the PPIase of interest. Peptides that specifically bind to the PPIase of interest can be further evaluated for PPIase inhibiting activity as described herein.

The phosphoserine and phosphothreonine-specific peptidyl-prolyl isomerase inhibitors, or PPIase inhibitors, of the present invention can comprise a core sequence of xSer/Thr-Y wherein x can be any negatively charged tetra- or penta-valent moiety and Y can be Pro or any Pro analog. Preferred moieties for x can be phosphate, sulfonate, boronate, phosphonate or a sulfonly amide. The Pro analog can be any nitrogen-containing ring structure, including imidazole, pyrole, tropolone, benzene, camphor, and heterocyclic aromatic and non-aromatic ring structures. Typically, the xSer/Thr-Y core sequence is flanked by hydrophobic residues or Arg, where the hydrophobic residues (e.g., Phe, Tyr, Trp and Ile) typically precede the xSer/Thr residue and Arg follows the Y residue. Specifically encompassed by the present invention are inhibitors comprising the core sequence phosphoserine/phosphothreonine-proline.

The inhibitors of the present invention can be anywhere from 2 to 200 amino acid residues in length. The inhibitors are typically 2–20 residues in length, and more typically 2–10 residues in length. Most typically the PPIase inhibitors are about eight residues in length, as represented by the consensus sequence, XXXpSer/pThrXXX (SEQ ID NO.:54), wherein X can be any amino acid residue.

Encompassed by the present invention are compounds that are about eight amino acid residues in length and comprise the core sequence $X_1X_2X_3pS-PX_4X_5X_6$ (SEQ ID NO.:1), wherein each residue can be independently selected as follows $X_1$ is W, Y or F; $X_2$ is F or I; $X_3$ is Y, R, F or W; $X_4$ is R, F, Y or W; $X_5$ is L or I and $X_6$ is any amino acid.

Specifically encompassed by the present invention is the inhibitor of a phosphoserine- or phosphothreonine-proline-specific peptide prolyl isomerase comprising Trp-Phen-Tyr-pSer-Pro-Arg (SEQ ID NO.:26).

The inhibitors of the present invention can be synthesized using standard laboratory methods that are well-known to those of skill in the art, including standard solid phase techniques. Inhibitors comprising naturally occurring amino acids can also be produced by recombinant DNA techniques known to those of skill, and subsequently phosphorylated.

The inhibitors of the present invention can comprise either the 20 naturally occurring amino acids or other synthetic amino acids. Synthetic amino acids encompassed by the present invention include, for example, naphthylalanine, L-hydroxypropylglycine, L-3,4-dihydroxyphenylalanyl, α-amino acids such as L-α-hydroxylysyl and D-α-methylalanyl, L-α-methyl-alanyl, β amino-acids such as β-analine, and isoquinolyl.

D-amino acids and other non-naturally occurring synthetic amino acids can also be incorporated into the inhibitors of the present invention. Such other non-naturally occurring synthetic amino acids include those where the naturally occurring side chains of the 20 genetically encoded amino acids (or any L or D amino acid) are replaced with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4,6, or 7 members can be employed.

As used herein, "lower alkyl" refers to straight and branched chain alkyl groups having from 1 to 6 carbon atoms, such as methyl, ethyl propyl, butyl and so on. "Lower alkoxy" encompasses straight and branched chain alkoxy groups having from 1 to 6 carbon atoms, such as methoxy, ethoxy and so on.

Cyclic groups can be saturated or unsaturated, and if unsaturated, can be aromatic or non-aromatic. Heterocyclic groups typically contain one or more nitrogen, oxygen, and/or sulphur heteroatoms, e.g., furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. The heterocyclic groups can be substituted or unsubstituted. Where a group is substituted, the substituent can be alkyl, alkoxy, halogen, oxygen, or substituted or unsubstituted phenyl. (See U.S. Pat. No. 5,654,276 and U.S. Pat. No. 5,643,873, the teachings of which are herein incorporated by reference).

Biologically active derivatives or analogs of the above-described inhibitors, referred to herein as peptide mimetics, can be designed and produced by techniques known to those of skill in the art. (See e.g., U.S. Pat. Nos. 4,612,132; 5,643,873 and 5,654,276, the teachings of which are herein incorporated by reference). These mimetics are based on a specific peptide PPIase inhibitor sequence and maintain the relative positions in space of the corresponding peptide inhibitor. These peptide mimetics possess biologically activity (i.e., PPIase inhibiting activity) similar to the biological activity of the corresponding peptide compound, but possess a "biological advantage" over the corresponding peptide inhibitor with respect to one, or more, of the following properties: solubility, stability, and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor. The following are examples of modifications of peptides to produce peptide mimetics as described in U.S Pat. Nos: 5,643,873 and 5,654,276, the teachings of which are incorporated herein by reference.

MODIFICATION OF THE N-AMINO TERMINUS

After solid phase synthesis of the peptide inhibitor, the blocking group on the N-terminus amino group can be selectively removed so as to provide for a peptide sequence blocked at all positions other than the N-terminal amino group and attached to a solid resin through the C-terminus.

One can then modify the amino terminus of the peptides of the invention to produce peptide mimetics of the invention.

Amino terminus modifications include alkylating, acetylating, adding a carbobenzoyl group, forming a succinimide group, etc. Specifically, the N-terminal amino group can then be reacted as follows:

(a) to form an amide group of the formula RC(O)NH— where R is as defined above by reaction with an acid halide (e.g., RC(O)Cl) or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to a scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkylamide group of the formula RC(O)NR—;

(b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane). See, for example, Wollenberg, et al., U.S. Pat. No. 4,612,132 which is incorporated herein by reference in its entirety. It is understood that the succinic group can be substituted with, for example, $C_2$-$C_6$ alkyl or -SR substituents which are prepared in a conventional manner to provide for substituted succinimide at the N-terminus of the peptide. Such alkyl substituents are prepared by reaction of a lower olefin ($C_2$-$C_6$) with maleic anhydride in the manner described by Wollenberg, et al., supra. and —SR substituents are prepared by reaction of RSH with maleic anhydride where R is as defined above;

(c) to form a benzyloxycarbonyl-NH— or a substituted benzyloxycarbonyl-NH-group by reaction with approximately an equivalent amount or an excess of CBZ—Cl (i.e., benzyloxycarbonyl chloride) or a substituted CBZ—Cl in a suitable inert diluent (e.g., dichloromethane) preferably containing a tertiary amine to scavenge the acid generated during the reaction;

(d) to form a sulfonamide group by reaction with an equivalent amount or an excess (e.g., 5 equivalents) of R—S(O)$_2$Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes);

(e) to form a carbamate group by reaction with an equivalent amount or an excess (e.g., 5 equivalents) of R—OC(O)Cl or R—OC(O)OC$_6$H$_4$—p—NO$_2$ in a suitable inert diluent (e.g., dichloromethane) to convert the terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); and (f) to form a urea group by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

MODIFICATION OF THE C-TERMINUS

In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

In preparing peptide mimetics wherein the C-terminal carboxyl group is replaced by the amide —C(O)NR$^3$R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides. Alternatively, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

MODIFICATION TO INCORPORATE A NON-PEPTIDYL LINKAGE

Peptide mimetics wherein one or more of the peptidyl linkages [—C(O)NH—] have been replaced by such linkages as a —CH$_2$— carbamate linkage, a phosphonate linkage, a —CH$_2$— sulfonamide linkage, a urea linkage, a secondary amine (—C$_2$NH—) linkage, and an alkylated peptidyl linkage [—C(O)NR$^6$—where R$^6$ is lower alkyl] are prepared during conventional peptide synthesis by merely substituting a suitably protected amino acid analogue for the amino acid reagent at the appropriate point during synthesis.

Suitable reagents include, for example, amino acid analogs wherein the carboxyl group of the amino acid has been replaced with a moiety suitable for forming one of the above linkages. For example, if one desires to replace a —C(O)NR— linkage in the peptide with a —CH$_2$— carbamate linkage (—CH$_2$OC(O)NR—), then the carboxyl (—COOH) group of a suitably protected amino acid is first reduced to the —CH$_2$OH group which then converted by conventional methods to a —OC(O)Cl functionality or a para-nitrocarbonate —OC(O)O—C$_6$H$_4$p—NO$_2$ functionality. Reaction of either of such functional groups with the free amine or an alkylated amine on the N-terminus of the partially fabricated peptide found on the solid support leads to the formation of a —CH$_2$OC(O)NR— linkage. For a more detailed description of the formation of such —CH$_2$— carbamate linkages.

Similarly, replacement of an amino linkage in the peptide with a phosphonate linkage can be achieved using techniques known to those of skill in the art.

Replacement of an amino linkage in the peptide with a —CH$_2$— sulfonamide linkage can be achieved by reducing the carboxyl (—COOH) group of a suitably protected amino acid to the —CH$_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH$_2$—S(0)$_2$Cl functional group which replaces the carboxyl group of the otherwise suitably protected amino acid. Use of this suitably protected amino acid analogue in peptide synthesis provides for inclusion of an —CH$_2$S(O)$_2$NR— linkage which replaces the amino linkage in the peptide thereby providing a peptide mimetic.

Replacement of an amino linkage in the peptide with a urea linkage can be achieved using techniques known to those of skill in the art.

Secondary amine linkages wherein a —CH$_2$NH— linkage replaces the amino linkage in the peptide can be prepared by employing, for example, a suitably protected dipeptide analogue wherein the carbonyl bond of the amino linkage has been reduced to a CH$_2$ group by conventional methods. For example, in the case of diglycine, reduction of the amide to the amine will yield after deportection H$_2$NCH$_2$CH$_2$NHCH$_2$COOH which is then used in N-protected form in the next coupling reaction. The preparation of such analogues by reduction of the carbonyl group of the amino linkage in the dipeptide is well known in the art.

The suitably protected amino acid analog is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is disopropylethylamine which is typically employed in about 10 fold excess. The reaction results in incorporation into the peptide mimetic of an amino acid analogue having a non-peptidyl linkage. Such substitution can be repeated as desired such that from zero to all of the amino bonds in the peptide have been replaced by non-amino bonds.

The inhibitors of the present invention can also be cyclic protein, peptides and cyclic peptide mimetics. Such cyclic inhibitors can be produced using known laboratory techniques, e.g., as described in U.S. Ser. No. 08/864,392, filed on May 28, 1997, the teachings of which are herein incorporated in their entirety by reference, and U.S Pat. No: 5,654,276, the teachings of which are herein incorporated in their entirety by reference).

Inhibitors of the present invention are evaluated for biological activity as described herein. For example, the candidate compounds can be screened in an assay that determines the displacement of a labeled high affinity molecule (e.g., a competitive inhibition asay) in an assay utilizing immobilized molecules on a grid, as well as screening libraries of candidate molecules. These techniques are known to those of skill in the art.

As defined herein, biological activity of the PPIase inhibitors include specific binding to the PPIase of interest (e.g., specific binding to Pin1) and/or specific inhibition of the peptidyl prolyl isomerase activity as measured as described in Schutkowski, M. et al., *Biochemistry*, 34:13016 (1995). Specific binding to the PPIase of interest can be determined as described herein. Further evaluation of candidate inhibitors (e.g., inhibitors that specifically bind to the PPIase of interest, for inhibiting activity can be determined by competitive inhibition assay. Alternatively, candidate moleucules of the present invention can be directly evaluated for their inhibitory activity withour prior determination of their specific binding to the isomerase of interest. Inhibitor compounds of the present invention typically have a K$_i$ in the nanomolar or micromolar range. Methods to determine K$_i$ are known to those of skill in the art.

The inhibitors of the present invention can be used in vitro to study cell cycle regulation and mitotic events. For example, the inhibitors of the present invention can be used to evaluate mitotic events in mammalian cells by inhibiting a specific isomerase and evaluating the effects on the cell cycle.

The inhibitors of the present invention can also be used to interfere with eucaryotic cell growth. The inhibitors can be used to inhibit cell growth, and to kill targeted cells. For example, the inhibitors of the present invention can be used to treat fungal and yeast, including Aspergillus, and parasitic infections (e.g., malaria) in mammals. As defined herein, mammals include domesticated animals and humans. Specifically, the inhibitors of the present invention can be used to treat hyperplastic and neoplastic disorders in mammals, including humans.

For example, Pin1 is an important molecule in controlling the sequential events of mitosis (FIG. 1). Entry and exit from mitosis are accompanied by abrupt changes in kinase activities, which lead to changes in the phosphorylation state of numerous proteins that trigger specific events in mitosis. Pin1 binding and consequent inhibition of target protein activity may provide a means for temporally synchronizing and/or amplifying the activity of mitotic proteins. Inhibition of Pin1 induces mitotic arrest and apoptosis. Thus, the Pin1 mediated mechanism of regulating mitotic events is a therapeutic target for cancer.

Neoplastic and hyperplastic disorders include all forms of malignancies, psoriasis, retinosis, athrosclerosis resulting from plaque formation, leukemias and benign tumor growth. For example, such disorders include lymphomas, papilomas, pulmonary fibrosis, rheumatoid arthritis and multiple sclerosis.

The inhibitors of the present invention can be formulated into compositions with an effective amount of the inhibitor as the active ingredient. Such compositions can also comprise a pharmaceutically acceptable carrier, and are referred to herein as pharmaceutical compositions. The inhibitor compositions of the present invention can be administered intraveneously, parenterally, orally, by inhalation or by suppository. The inhibitor composition may be administered in a single dose or in more than one dose over a period of time to achieve a level of inhibitor which is sufficient to confer the desired effect.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsiers, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

It will be appreciated that the actual effective amounts of the inhibitor in a specific case will vary according to the specific compound being utilized, the particular composition formulated, the mode of administration and the age, weight and condition of the patient, for example. As used herein, an effective amount of inhibitor is an amount of inhibitor which is capable of inhibiting the isomerase activity of the isomerase of interest, thereby inhibiting target cell growth and resulting in target cell death. Dosages for a particular patient can be determined by one of ordinary skill in the art using conventional considerations, (e.g. by means of an appropriate, conventional pharmacological protocol).

The present invention is illustrated by the following examples, which are not intended to be limited in any way.

EXAMPLE 1

Expression, Purification and Kinetic Analysis of Recombinant Pin1 Proteins

Pin1 was expressed and purified by $Ni^{2+}$-NTA agarose column as an N-terminally $His_6$-tagged fusion protein, followed by removing the tag using thrombin, as described in Lu et al., 1996; and Ranganathan et al., 1997). To generate an N-terminally GST-Pin1 fusion protein, Pin1 cDNA was subcloned into a pGEX vector and the resulting fusion protein was expressed and purified by glutathione agarose column, as described in Lu et al., 1993; Lu, et al., 1996. GST-Pin1 was stored in the agarose bead at 4° C. for 2 weeks or eluted from the beads and concentrated to 20 mg/ml with a Centricon-10 (Amicon), followed by storing at −80° C. Both preparations were stored in a buffer containing 20 mM HEPES, pH 7.5, 50 mM NaCl and 1 mM DTT, as described in Ranganathan et al., 1997. All proteins were quantified by the method of Bradford (Biorad) using BSA as a standard.

Site-directed mutations of Pin1 were introduced using PCR-based techniques and verified by DNA sequencing. The corresponding mutant proteins were expressed and purified using the same procedures as those described for wild-type Pin1. PPIase activity was measured, as described previously (Lu et al., 1996), with the exception that the absorbance of p-nitroaniline (at 395 nM) was followed every second for 2–10 min. and data were analyzed offline using a kinetic computer program written by G. Tucker-Kellogg in the C. Walsh lab at Harvard Medical School.

EXAMPLE 2

Analysis of Pin1 and Its Binding Proteins During Cell Cycle

HeLa cells were arrested at the G1/S boundary using double thymidine and aphidicolin block, and released to enter the cell cycle, as described in Heintz, N., H. L. Sive and R. G. Roeder, Mol Cell Biol 3:539–550 (1983) and Lu, K. P. and T. Hunter, Cell 81:413–424 (1995)). To accumulate cells at mitosis, nocodazole (50 ng/ml) was added to cells at 8 h after the release for the specified period of time. To obtain a large quantity of interphase and mitotic cells, HeLa cells were incubated with double thymidine and aphidicolin or nocodazole for 16 h, which resulted in over 90% of cells being arrested at the G1/S boundary or mitosis, respectively. Cells were harvested and a aliquot of cells was subjected to flow cytometry analysis, as described in Lu and Hunter, 1995). The remaining cells were lysed in RIPA buffer (10 mM sodium phosphate pH 7.4, 150 mM NaCl, 1% NP-40, 1% sodium deoxycholate, 0.1% SDS, 50 mM NaF, 1 mM sodium orthovanadate, 10 µg/ml aprotinin, 50 µg/ml phenylmethylsulfonyl fluoride and 1 mM DTT) and same amount of total proteins were subjected to immunoblotting analysis using various antibodies or Farwestern analysis using GST-Pin1 as a probe. For Farwestern analysis, after blocking with 5% BSA, membranes were incubated with 2 µg/ml GST-Pin1 in TBST for 2 hr, followed by incubation with anti-GST monoclonal antibodies (UBI) and the ECL detection procedures.

EXAMPLE 3

Microinjection of xenopus Embryos

Figure 2:
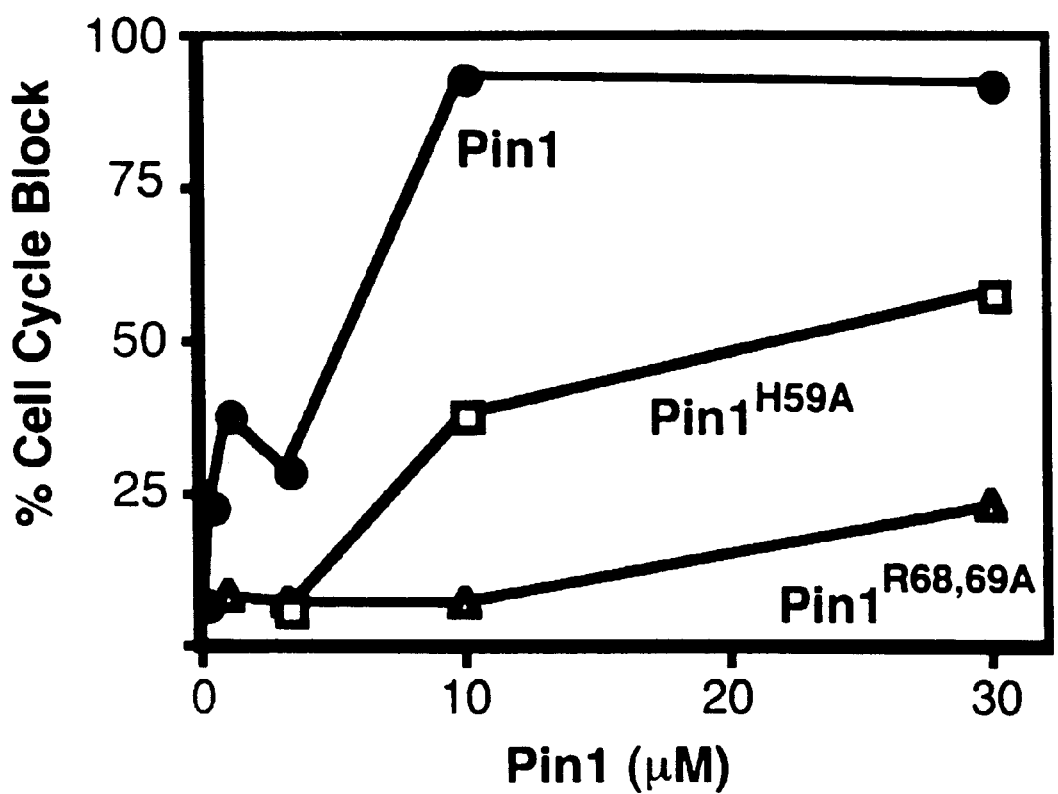
FIG. 2 is a graphic representation of the results of an experiment showing that Pin1 inhibits mitotic division in Xenopus embryos.

Unfertilized eggs were incubated with sperm, dejellied, and 4 µM of the indicated protein (about 10 fold above the estimated endogenous levels) was injected in one cell of two cell stage embryos (30 embryos each protein). The injected embryos were allowed to develop at 18° C. to stage 8 and pictures were taken of typical embryos. The titration of Pin1 and the mutants was essentially as described above except that the indicated protein was injected into one cell of 4 cell stage (18 embryos each Pin1 concentration) to the indicated final concentration and allowed to develop for 3h. The cell cycle blocks by GST-Pin1 were not homogeneous as cells that were injected with greater concentrations of GST-Pin1 were cleaved fewer times indicating a tighter cell cycle block. To be consistent, cell cycle blocked embryo's were scored as those that contained at least one cell on the injected side that was greater than 5 times larger than uninjected cells (FIG. 2).

EXAMPLE 4

Preparation of Xenopus CSF Extracts

Xenopus CSF extracts were prepared from unfertilized eggs, as previously described (Murray, 1991) and used immediately. To examine the effect of Pin1 on mitotic entry, a fresh CSF extract containing demembranated sperm (150/µl) and rhodamine tubulin (2 µg/ml) was activated by addition of 0.4 mM calcium chloride for 15 min, before the indicated concentrations of various Pin1 proteins were added and mitotic entry was followed for 2 h by nuclear morphology, nuclear envelope breakdown, spindle formation and Cdc2 activity, as described previously (Murray, A. W., Methods Cell Biol 36:581–605 (1991)). The cell cycle state of nuclei within the extracts were over 90% synchronous and typical nuclei were photographed.

EXAMPLE 5

Synthesis of Mitotic Phosphoproteins

The mitotic phosphoproteins were translated in vitro using the TNT coupled transcription/translation kit (Promega) in a total volume of 10 µl in the presence of 8 µCi [$^{35}$S]methionine (1000 Ci/mmol) for 2 h at 30° C. They were then incubated in xenopus interphase and mitotic extracts as described (Stukenberg et al., 1997). These incubated clones were precipitated by Pin1 beads as described below. The Xenopus Mos and Wee1 clones were a kind gift of M. Murakami, G, F. Woude and J. Cooper; the Xenopus Cdc25 clone was a generous gift of W. Dunphy, T3 and T3S2 Cdc25 mutants were kindly provided by J. Maller (Izumi and Maller, 1993).

EXAMPLE 6

Production of Pin1 and Cdc25 Antibodies

Since antibodies that we previously raised against C-terminal peptide of Pin1 (Lu, et al., 1996) did not have a high sensitivity for detecting Pin1, especially for Xenopus Pin1, rabbits were immunized with His-Pin1 as an antigen. After 2 months, antisera specifically recognize a single 18 kDa Pin1 protein in human cells and Xenopus extracts.

To raise antibodies against Xenopus Cdc25, recombinant GST-Cdc25 (the clone was a kind gift of A. Nebrada and T. Hunt) was affinity purified as described by the manufacture (Pharmacia). The protein was further purified by SDS-PAGE and a gel slice containing Cdc25 was used to immunize rabbits.

EXAMPLE 7

GST Pull-down, Imunoprecipitation and Immunoblotting Analysis

To detect Pin1-binding proteins, either HeLa cells were lysed in or Xenopus extracts were diluted in a buffer (buffer A) containing 50 mM Tris-HCl, pH 8.0, 200 mM NaCl, 100 mM NaF, 1 mM sodium orthovanadate, 10% glycerol, 1% Triton X100, 10 µg/ml aprotinin, 50 µg/ml phenylmethylsulfonyl fluoride and 1 mM DTT. The lysates were preclarified with boiled S. aureus bacteria (CalBiochem) and then incubated with 10 µl of agarose beads containing various GST-Pin1 proteins or control GST for 2 h at 4° C. The precipitated proteins were washed 5 times in the same buffer and subjected to immunoblotting analysis. Immunoprecipitation and immunoblotting analysis using MPM-2 antibody (Davis et al. 1983), which was kindly provided by J. Kuang, Pin1 antibodies (Lu et al., 1996, kindly provided by M. White or newly generated), anti-phospho.Tyr antibody (UBI), anti-Cdc25C (Ogg, et al., 1994) (from H. Piwnica-Worms and Santa Cruz Biotechnology), anti-Cdc27, anti-Plk1 (Zymed), anti-Cdc2 (Solomon, M. J., M. Glotzer, T. H. Lee, M. Philippe and M. W. Kirschner. Cell 63:1013–1024 (1991), anti-human Myt1, anti-human cyclin B1 and anti-Xenopus cyclin B were performed, as described previously in Lu and Hunter, 1995; Lu et al., 1996).

EXAMPLE 8

Coimmunoprecipitation of Pin1 and Cdc25

To detect Pin1 and Cdc25 interaction during the Xenopus cell cycle, about 500 eggs were fertilized in a minimal volume of MMR (100 m NaCl, 2 mM KCl, 1 mM MgCl2, 2 m CaCl2, 0.1 MM EDTA, 5 MM HEPES, pH 7.8), diluted in 0.1×MMR for 10 minutes, dejellied as described in Murray, (1991) and incubated in CSF-XB (100 mM KCl, 0.1 mM CaCl2, 2 mM MgCl2, 10 mM K-HEPES, pH 7.7, 50 mM Sucrose 5 mM EGTA, pH 7.7). At the indicated time after fertilization 15 eggs were crushed into 150 µl of ice cold CSF-XB with 1 µM okadeic Acid, microcenfuged for 20 seconds, the layer between the yolk and the pellet was removed to a fresh chilled tube. This solution was mixed well and 5 µl was frozen in liquid nitrogen for future H1 kinase assays, and 30 µl was diluted in 10 µl of either α-cdc25 or control rabbit sera beads in 100 µl of buffer A (containing 5 mM EDTA and 1 µM microcystein but not vanadate). The immunoprecipitation reactions were rotated for approximately 40 minutes at 4° C., washed 4 times in and subjected to immunoblotting with anti-Pin1 antibodies. The associated Pin1 was quantified as described (Stukenberg et al., 1997).

EXAMPLE 9

Cdc2 and Cdc25 Assays

Cdc2 was assayed using histone H1 as a substrate, as previously described in Murray, 1991; Lu and Hunter, (1995). Cdc25 activity was assayed by using the activation of its endogenous substrate, Cdc2/cyclin B complex phosphorylated on Thr161, Tyr15, Thr14 as an indicator using a variation of an established protocol (Kumagai, A. and W. G. Dunphy. 1996. Science 273:1377–1380 (1996). When cyclin B is added to a Xenopus interphase extract at levels insufficient to activate mitosis (referred to as a "subthreshold cyclin concentration"), the added cyclin B binds Cdc2 and the Cdc2 in the complex is phosphorylated by CAK, Wee1 and Myt 1 to accumulate in an inactive form (Solomon et al. 1991).

A subthreshold concentration of GST cyclin B (10 µg) was added to 1 ml of Xenopus interphase extract for thirty min at room temperature (Solomon, M. J., M. Glotzer, T. H. Lee, M. Philippe and M. W. Kirschner, Cell 63:1013–1024 (1990). This was diluted 8 fold in XB+3 mM DTT, rotated for 1 h with 3 ml of GST agarose beads, washed 3 times in XBIP (XB+500 mM NaCl and 1% NP40+2 mM DTT), washed 2 times (once overnight) in EB (80 mM β glycerol phosphate, 15 mM EGTA, 15 mM MgCl2)+2 mM DTT, 500 mM NaCl and 1% NP40, and finally twice with EB+10 mM DTT. These Cdc25 assay beads were stored at 4° C. for up to 1 month. Mitotic GST-Cdc25 was purified by incubating 22 µg of GST-Cdc25, in a Xenopus mitotic extract for 30 min at 23° C., this was diluted 8 fold in XB and rotated with 50 µl of glutathione-Agarose beads (Sigma) for 1 hr at 4° C. The beads were washed 5 times in XB-IP, twice in XB+2 mM DTT and eluted in 25 µl XB+2 mM reduced GSH. The final concentration of Mitotic GST-Cdc25 was 0.36 mg/ml. A 27 fold dilution of this mitotic GST-Cdc25 could fully activate Cdc2 in the assay below, while GST-cdc25 isolated from Interphase extracts in parallel lost activity after a 3 fold dilution. Thus the mitotic extract stimulated the Cdc25 at least 9 times over interphase extracts. To assay Cdc25 activity 1 µM mitotic GST-cdc25, and the indicated concentration of either Pin1, Pin1$^{R68,69A}$ or BSA were incubated in a 20 µl reaction in XB+1 mM ATP for 10 minutes at room temperature. These reactions were sequentially diluted (1/1, 1/3, 1/9, 1/27) into XB+1 mM ATP and 10 µl of each was mixed with 10 µl of cdc25 assay beads for 10 minutes at room temperature with constant shaking. The Cdc25 assay beads were washed 3 times in XB-IP, 2 times in EB+1 mM DTT and assayed for H1 kinase activity. Phosphoimager analysis of the H1 kinase assays were quantified by the Molecular Dynamics ImageQuant 3.3 software. As described herein an assay with 1 μM mitotic GST-cdc25, 0.67 μM of either Pin1, Pin1$^{R68,69A}$ or 16 μM BSA then diluted 27 fold before being mixed with the Cdc25 assay beads and the amount of H1 kinase activity is relative to the amount of activity of the beads without cdc25 being zero and the BSA reaction being 100%. The most reproducible way to quantify the Cdc25 activity in this assay was by determining the endpoint dilution of Cdc25 which could activate Cdc2. Therefore the Cdc25 activity is quantified by the endpoint dilution of the mitotic GST-Cdc25 at which Cdc2 on the beads could still be significantly activated.

EXAMPLE 10

Pin1 Levels are Constant through the Cell Cycle

Whereas overexpression of Pin1 results in G2 arrest, depletion of Pin1 induces mitotic arrest without affecting DNA synthesis. To determine the basis for this cell cycle-specificity, it was determined whether Pin1 protein level fluctuated during the cell cycle. To address this question, HeLa cells were synchronized at the G1/S boundary. At different times following the release from the block, cells were harvested and analyzed by flow cytometry or lysed and analyzed for protein expression by immunoblotting. Analysis of DNA content and cyclin B1 levels indicated that the HeLa cells synchronously progressed through different phases of the cell cycle. However, total Pin1 levels did not change significantly during the cell cycle.

EXAMPLE 11

Pin1 Directly Binds a Subset of Conserved Mitotic Phosphoproteins

Since the levels of Pin1 do not fluctuate during the cell cycle, its mitosis-specific function is likely conferred by some other mechanisms. There are many such possibilities. Pin1 could be subjected to post-translational modifications, such as phosphorylation, or allosteric interactions with a transiently appearing subunit, like a cyclin which regulates its activity. Alternatively, the interaction of Pin1 and its targets may be cell cycle-regulated. Initial experiments suggested no evidence for Pin1 phosphorylation or for interaction of Pin1 with a regulatory subunit. A cell cycle-dependent interaction of Pin1 with its binding proteins was tested for.

A glutathione-S-transferase (GST) fusion protein containing full length Pin1 was bacterially expressed, purified, and then used to probe for interacting proteins in S-phase, mitosis or G1-phase by Farwestern analysis. The ability of Pin1 to interact with cellular proteins remained relatively low during S, increased when cells progressed though G2/M (10 h point), and was almost completely lost when cells moved to the next G1 (14 h point). However, if cells were not allowed to progress into the next cell cycle, but rather were blocked at mitosis by adding nocodazole (14+Noc), Pin1-binding activity increased even further. Since the binding activity was detected using denatured proteins, the protein-protein interaction between Pin1 and these proteins must be direct.

To examine whether this Pin1 interaction with its target proteins occur under nondenaturing conditions and to estimate the number of Pin1-interacting proteins, glutathione beads containing GST and GST-Pin1 were incubated with interphase and mitotic extracts, and beads were extensively washed and proteins bound to beads were separated on SDS-containing gels and stained with Coomassie blue. Whereas GST did not precipitated any detectable proteins from either interphase or mitotic extracts, GST-Pin1 specifically precipitated about 30 clearly Coomassie-stainable bands from mitotic extracts, but only 4–7 minor bands from interphase extracts. Together, these two results indicate that Pin1 mainly interacts with a subset of proteins in a mitosis-specific manner.

The crystal structure of Pin1 suggests that Pin1 could strongly interact with a Phospho.Ser/Thr-Pro motif (Ranganathan, et al., *Cell* 89:875–886 (1997)). A large number of proteins have been shown to be phosphorylated at such a motif specifically during mitosis and many of these phosphoproteins are recognized by the MPM-2 antibody. Therefore, interactions between Pin1 and MPM-2 antigens were examined. After incubation with soluble proteins prepared from interphase and mitotic HeLa cells, GST-Pin1 and control GST glutathione beads were washed extensively and the interacting proteins are detected by immunoblotting with the MPM-2 antibody. Many of the GST-Pin1-binding proteins reacted with MPM-2 only in the mitotic extracts, including a strong band of 55 kDa (p55). p55 has been previously shown to be the most prominent MPM-2 antigen in HeLa cells (Zhao et al., *FEBS Lett* 249:389–395 (1989), although its identity remains to be determined. In contrast, control GST glutathione beads precipitated just two proteins (p58/60) from either lysate. In addition, when MPM-2 immunoprecipitates were subjected to Farwestern analysis using GST-Pin1 as a probe, Pin1 directly bound MPM-2 antigens on membranes.

To determine whether GST-Pin1 can deplete MPM-2 antigens and to estimate what concentrations of Pin1 are required to completely deplete MPM-2 antigens, mitotic extracts were incubated with different amounts of GST-Pin1, followed by analyzing MPM-2 antigens remaining in the depleted supernatants. The total cellular Pin1 concentration in HeLa cells was estimated to be about 0.5 μM, based on immunoblotting analysis using anti-Pin1 antibodies with recombinant Pin1 protein as a standard. At a concentration (8 μM) that was about 15 fold higher than the endogenous level, Pin1 depleted the majority of MPM-2 antigens, indicating that Pin1 strongly interacts with most MPM-2 antigens. The above results demonstrate that Pin1 interacts with MPM-2 antigens in vitro.

To determine if endogenous Pin1 interacts with MPM-2 antigens in the cell, Pin1 was immunoprecipitated from either interphase or mitotic HeLa extracts using anti-Pin1 antibodies in the presence of various phosphatase inhibitors. The resulting Pin1 immunoprecipitates were probed with MPM-2. As described above, several MPM-2 antigens were co-immunoprecipitated with anti-Pin1 antibodies. These results indicate that stable complexes between Pin1 and MPM-2 antigens exist in the cell and that Pin1 does not form complexes with all Pin1-binding proteins at the same time in vivo.

Since Pin1 and MPM-2 antigens are highly conserved, it is possible that Pin1-binding proteins are also conserved. To examine this possibility, the interaction between human Pin1 and mitotic phosphoproteins in Xenopus extracts was observed. When GST-Pin1 was incubated with interphase or mitotic egg extracts, Pin1 specifically precipitated a subset of MPM-2 antigens from mitotic extracts, with molecular weights similar, although not identical, to those present in human cells. Again, this interaction between Pin1 and Xenopus MPM-2 antigens was specific as it was not detected if the precipitation was performed with control GST glutathione beads. These results demonstrate that Pin1 also interacts with a subset of conserved mitosis-specific phosphoproteins in Xenopus.

EXAMPLE 12

Mutations in the Binding Pocket Abolish the Ability of Pin1 to Interact with Most Mitotic Phosphoproteins The above results demonstrate that Pin1 directly binds numerous conserved mitotic phosphoproteins in a mitosis-dependent manner. To insure that this interaction is highly specific for Pin1, site-specific mutations were introduced into Pin1. A high resolution X-ray structural and preliminary functional analysis of Pin1 suggest that a basic cluster consisting of Lys63, Arg68, and Arg69 is likely to be coordinate the putative phosphate group in the substrate. Ala substitutions at these residues (Pin1$^{R68,69A}$) should cause a reduction in the ability to bind phosphorylated residues N-terminal to the target Pro residue in the substrate. In addition, His59 has been shown to have an intimate contact with the cyclic side chain of the catalyzing Pro residue. An Ala substitution at His-59 of Pin1 (Pin1$^{H59A}$) should therefore disrupt the interaction between Pin1 and the substrate Pro residue.

The mutant proteins were expressed and purified as GST fusion proteins, and both their PPIase activity and their ability to bind mitotic phosphoproteins were determined. PPIase activity was assayed with two peptide substrates: AEPF, which has an acidic residue at the position N-terminal to the catalytic Pro residue, and AAPF, which does not. Pin1 had a strong preference for the AEPF substrate. The PPIase activity of Pin1$^{R68,69A}$ was reduced more than 90% against AEPF, whereas the reduction was very small against AAPF. Moreover, pin1$^{R68,69A}$ had little preference for either substrate. These results confirm that residues Arg68 and Arg69 are critical for promoting strong selection for a negatively charged residue at the position N-terminal to the substrate Pro residue. The PPIase activity of Pin1$^{H59A}$ was barely detectable against either peptide substrate, confirming the importance of His59 in Pin1 substrate binding and/or catalysis.

To determine if the Pin1 mutants interact with mitotic phosphoproteins, GST-Pin1, -Pin1$^{R68,69A}$ and -Pin1$^{H59A}$ fusion proteins were incubated with interphase or mitotic HeLa cell extracts and associated proteins subjected to MPM-2 immunoblotting analysis. Pin1 specifically interacted with MPM-2 antigens in two independently prepared mitotic extracts, but the binding activity of both Pin1$^{R68,69A}$ and Pin1$^{H59A}$ was significantly reduced compared to the wild-type protein. A few proteins including the most strongly reacting p55 band could still be recognized. The two Pin1 mutants also failed to bind most mitotic phosphoproteins from Xenopus extracts. Thus, mutating the residues that are implicated in binding either the substrate's putative phosphate group or the substrate's Pro residue abolish the ability of Pin1 to bind MPM-2 antigens. This suggests that Pin1 must recognize both the Phospho Ser/Thr and the Pro residues to bind MPM-2 antigens. These results also demonstrate that mitotic phosphoproteins specifically interact with active site residues of Pin1

EXAMPLE 13

Identification of Several Mitotic Regulators as Pin1 Targets

Several known mitotic regulators such as cyclin B, Cdc25, Myt1, Plk1 and Cdc27 are phosphorylated at mitosis. To identify at least a few of the many Pin1 binding proteins, Pin1-binding proteins were precipitated from HeLa cells, or Xenopus extracts and probed with antibodies specific for known mitotic phosphoproteins. As shown previously, levels of Plk1 and cyclin B1 increased at mitosis, whereas similar amounts of Cdc25C were present in interphase and mitotic HeLa cells. Moreover, a significant fraction of Cdc25C, Plk1, Myt1, Cdc27 and PTP-1B became hyperphosphorylated during mitosis and exhibited a shift in electrophoretic mobility by SDS-PAGE. Although cyclin B1 and PTP-1B were not precipitated by Pin1 in either interphase or mitotic extracts, Pin1 bound selectively only to the mitotically hyperphosphorylated form of Cdc25C, Plk1, Myt1 and Cdc27. Furthermore, neither mutant Pin1$^{R68,69A}$ nor Pin1$^{H59A}$ interacted with Cdc25 or Cdc27, indicating that the residues that are implicated in binding either the substrate's putative phosphate group or the substrate's Pro residue are necessary for Pin1 to bind Cdc25 and Cdc27. Similarly, only the mitotic, but not the interphase form of Xenopus Cdc27 was precipitated by Pin1. Moreover, pretreatment of the mitotic extract with calf intestine phosphatase (CIP) completely dephosphorylated Cdc27 and abolished the interaction between Pin1 and Cdc27, demonstrating a phosphorylation-dependent interaction. These results indicate that the interaction between Pin1 and Cdc25 or Cdc27 is likely to be mediated by a Phospho.Ser/Thr-Pro motif.

To gain a sense of the generality of the interaction between Pin1 and mitotic phosphoproteins and to confirm the Pin1 interaction with target proteins is indeed mediated by phosphorylation, the ability of Pin1 to bind other known mitotic phosphoproteins and a set of mitotic phosphoproteins identified by a systematic phosphoprotein screen (Stukenberg et al., Curr Biol 7:338–348 (1997). Proteins synthesized in vitro were phosphorylated in a cell cycle specific manner by incubating them in either Xenopus interphace or mitotic extracts. These labeled protein were subsequently incubated with GST-Pin1 beads that were extensively washed and the bound proteins analyzed by SDS-PAGE. To validate this method, Cdc25 was first tested. Again, the mitotically phosphorylated form of in vitro translated Cdc25 could be precipitated by GST-Pin1 beads. However, Cdc25 was not recognized by Pin1 if it was incubated in interphase extracts. Moreover, Pin1 did not interact with Cdc25 if the mitotically phosphorylated Cdc25 was treated with phosphatase prior to the GST-Pin1 incubation. These results demonstrate that this method can be used to detect mitosis-specific and phosphorylation-dependent interactions between Pin1 and phosphoproteins. Out of the 13 mitotic phosphoproteins examined, Pin1 bound 10 in a mitosis and phosphorylation-dependent manner (summarized in Table 1), including Wee1, MP75 and MP110, MP75 and MP110 are Xenopus proteins related to microtubule-associated protein E-MAP-115 and the fission yeast G2 transcription factor Cdc5, respectively. These results indicate that Pin1 may target many mitosis-specific phosphoproteins.

EXAMPLE 14

Pin1 Blocks Cell Cycle Progression in Xenopus Embryos and Entry into Mitosis in Xenopus Extracts Since Pin1 is conserved from yeast to humans, it is likely that Pin1 exists in xenopus. To confirm this, Xenopus egg extracts were immunoblotted with two separate anti-human Pin1 antisera. Both antibodies, but not their respective preimmune sera, specifically recognized a band which comigrated with human Pin1 at 18 kDa, indicating that Pin1 is present in Xenopus.

Overexpression of Pin1 has been shown to inhibit cell cycle progression in both yeast and HeLa cells. To examine whether increasing the concentration of Pin1 has similar biological effects in Xenopus, Pin1 or Pin1 mutants were injected into one cell of 2 cell stage embryos and allowed the embryos to develop for 3 h (about 5 divisions). Wild-type Pin1 injected cells failed to cleave or cleaved slowly when compared to the cells in the uninjected side. A similar concentration (4 $\mu$M final) of either Pin1 mutant had little effect on the cell cycle. In a separate experiment Pin1 blocked cleavage of the injected cells in a concentration-dependent manner, and at a concentration approximately 20 fold above the estimated endogenous levels (10 $\mu$M), completely inhibited the cell cycle (FIG. 1). In contrast, higher concentrations of the mutant proteins were needed to block the cell cycle (FIG. 1). Injection of control BSA had no obvious effect on cell cycle progression. These results suggest that Pin1 must bind mitotic phosphoproteins in order to block cell cycle progression. To determine the nature of the cleavage block in Xenopus, GST-Pin1 was added to Xenopus egg extracts that had been arrested in second meiotic metaphase due to the activity of cytostatic factor. These extracts are arrested in mitosis (meiosis II) and reenter the cell cycle in response to the addition of $Ca^{2+}$. Extracts containing demembranated sperm to monitor nuclear morphology and rhodamine-tubulin to monitor microtubule spindle assembly, were activated with Ca Pin1 was added after the extracts had entered interphase (15 min after the addition of $Ca^{2+}$), and the subsequent entry of the extracts into mitosis was followed by nuclear morphology and Cdc2 kinase activity using histone H1 as a substrate. Addition of either 10 or 40 $\mu$M Pin1, approximately 20 or 80 fold higher than endogenous levels, completely blocked entry into mitosis as detected by the persistence of interphase nuclei and low Cdc2 kinase activity. In contrast, the same extracts containing 40 $\mu$M of either BSA or the mutant Pin1 proteins entered mitosis by 70 to 80 min as detected by nuclear envelope breakdown, spindle formation and high histone H1 kinase activity. Thus, as was shown previously in HeLa cells, increasing the Pin1 concentration causes a cell cycle block in G2. More importantly, Pin1 must bind mitotic phosphoproteins to elicit this phenotype.

EXAMPLE 15

Pin1 Binds and Inhibits Mitotically Phosphorylated Cdc25

The above results indicate that overexpression of Pin1 inhibits mitotic entry in Xenopus, as is the case in HeLa cells and yeast. Entry into mitosis is regulated by dephosphorylation of Cdc2 by the phosphatase Cdc25, and Cdc25 is activated by mitosis-specific phosphorylation at the MPM-2 epitope at the G2/M transition. Earlier results indicated that it is the mitotically phosphorylated form of Cdc25 that interacts with Pin1 in vitro. Therefore, it is conceivable that the inhibitory effects of Pin1 on entry into mitosis could at least partially explained through inhibition of Cdc25 activity.

To test this possibility, it was determined whether Pin1 interacts with Cdc25 in vivo and if so, whether this interaction is cell cycle regulated. Xenopus eggs were collected at various times after fertilization and subjected to immunoprecipitation using anti-Xenopus Cdc25 antibodies as well as histone H1 kinase assay to monitor cell cycle progression. When the resulting Cdc25 immunoprecipitates were immunoblotted with anti-Pin1 antibodies, we found that endogenous Pin1 was precipitated by anti-Cdc25 antibodies. Furthermore, this interaction between Pin1 and Cdc25 was cell cycle-regulated, significantly increased just prior to mitosis. Similar results were also obtained using synchronized HeLa cells using anti-human Cdc25C. Unfortunately, we were not able to detect Cdc25 in anti-Pin1 immunoprecipitates, probably because the amount of Cdc25 precipitated is below the detection of the Cdc25 antibodies. It is worth of pointing out that the percentage of coimmunoprecipitatable Pin1 and phosphorylated Cdc25 is not high. This might be expected because the complex might not be stable to the stringent immunoprecipitation conditions, the amount of Cdc25 phosphorylated on Pin1-binding sites might be low at this point, and/or the complex might have a high off rate, since the phosphorylated Cdc25 is a substrate of Pin1. Nevertheless, these results suggest that Pin1 is associated with Cdc25 at a time when Cdc25 is partially phosphorylated and yet its activity is low.

Since the interaction between Pin1 and Cdc25 is mediated by phosphorylation of Cdc25, it was determined whether Pin1 interacts with Cdc25 on important phosphorylation sites. At entry into mitosis, Cdc25 is phosphorylated at multiple Thr/Ser-Pro (Peng, C. Y. Graves, P. R., Thoma, R. S. Wu, Z. Shaw, A. S. and Piwnica-Worms, H. *Science*, 277:1501–1505 (1997)).

Izumi and Maller (Izumi, T. and J. L. Maller, *Mol Biol Cell* 4:1337–1350 (1993)) have shown that the triple mutation of conserved Thr48, Thr67 and Thr138 (T3 Cdc25), and the quintuple mutation of the three Thr residues plus Ser205 and Ser285 (T3S2 Cdc25) prevent most of the shift in electrophoretic mobility of Cdc25 after incubation with mitotic extracts. When they measured the ability of the Cdc25 mutants to activate Cdc2 in the Cdc25-depleted oocyte extracts and to initiate mitotic entry in oocyte extracts, the activities of T3 and T3S2 mutants were reduced about 70% and 90%, respectively (Izumi and Maller, 1993). These results indicate that these Thr/Ser residues are essential for the Cdc25 function. We examined the ability of Pin1 to bind the T3 and T3S2 Cdc25 mutants. As shown previously (Izumi and Maller, 1993), the T3 and T3S2 Cdc25 mutants failed to undergo the mobility shift after incubation with mitotic extracts. Although Pin1 strongly bound mitotically phosphorylated form of Cdc25, Pin1 almost (T3) or completely (T3S2) failed to bind the Cdc25 mutants which were incubated with either interphase or mitotic extracts. Although further experiments are required to pinpoint which phosphorylation site(s) play(s) the major role in mediating the Pin1 and Cdc25 interaction, these results show that Pin1 interacts with the phosphorylation sites on Cdc25 that are essential for its mitotic activation.

Figure 3A:
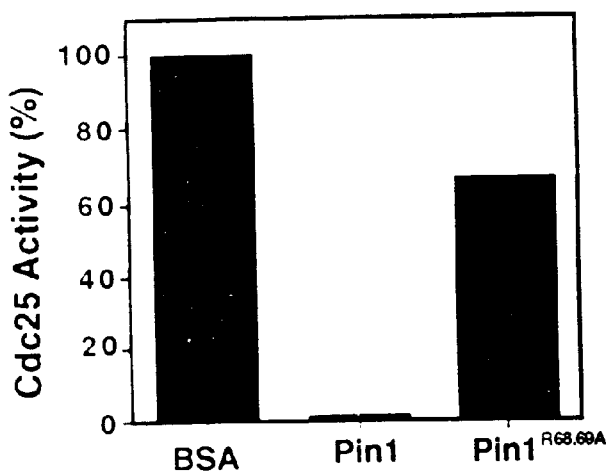
FIGS. 3A–C are graphic representations showing that Pin1, but not the mutant, directly inhibits the ability of Cdc25 to activate cyclin B/Cdc2.
Figure 3B:
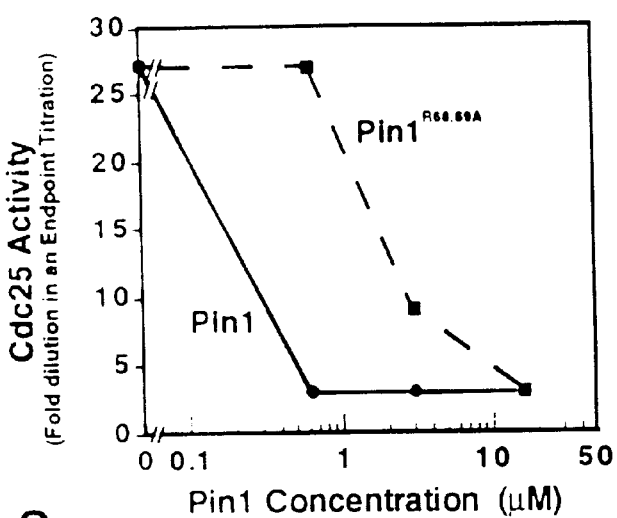
Figure 3C:
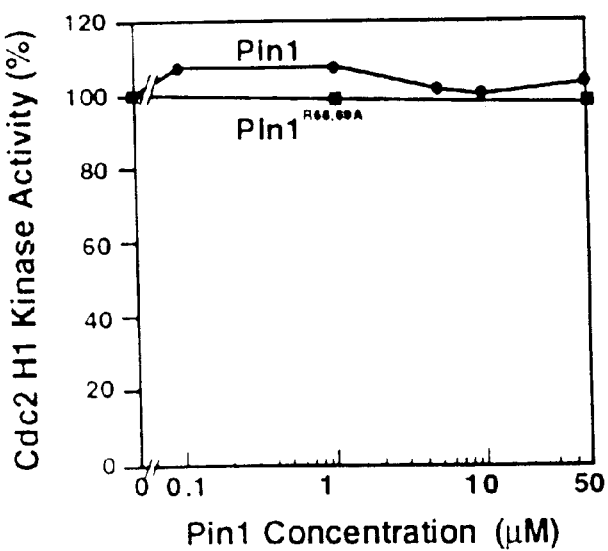

The above results indicate that Pin1 interacts with Cdc25 both in vitro and in vivo. Therefore, we tested whether Pin1 could affect the physiological activity of Cdc25, which is to dephosphorylate and activate the cyclin B/Cdc2 complex. To generate the mitotically phosphorylated form of Cdc25, GST-Cdc25 was incubated in Xenopus mitotic extracts, affinity purified on glutathione agarose beads and eluted. This mitotic Cdc25 was at least 9 fold more active than GST-Cdc25 purified in parallel from interphase extracts (data not shown). This mitotic GST-Cdc25 activated cyclin B/Cdc2 complex that was kept inactive due to inhibitory phosphorylations on Tyr15 and Thr14. If Pin1 (0.67 $\mu$M) was included in the assay at amounts approximately stoichiometric to mitotic Cdc25 (1 $\mu$M), mitotic Cdc25 failed to activate the Cdc2 complex. In contrast, neither the mutant Pin1$^{R68,69A}$ at the same concentration (0.67 μM), or BSA at a 25 fold higher concentration (15 μM) had a significant inhibitory effect on Cdc25 activity (FIG. 3A). Five fold higher concentrations of Pin1$^{R68,69A}$ could partially inhibit mitotic Cdc25 activity (FIG. 3B), a result which is consistent with the requirement for higher concentrations of this mutant protein to arrest the Xenopus cell cycle. To rule out the possibility that Pin1 could directly inhibit the cyclin B/Cdc2 complex itself, we examined the effect of Pin1 and its mutants on the activity of dephosphorylated-active cyclin B/Cdc2 under same conditions. Neither Pin1 nor the Pin1 mutant had any effect on cdc2 activity (FIG. 3C). Taken together, these results indicate that Pin1 could inhibit premature mitotic activation of Cdc25 by interacting with the phosphorylation sites on Cdc25 that are essential for its activation. This offers one explanation for the ability of Pin1 to inhibit mitotic entry.

EXAMPLE 16

Screening of Peptide Libraries

The oriented peptide library approach (Z. Songyang et al. Cell, 72:767 (1993) was used to screen for optimal peptides. All amino acids except C were incorporated at equimolar amounts in each degenerate position, yielding a total theoretical degeneracy for both libraries of $19^6=4.7\times10^7$ distinct peptide sequences. Pin1-GST beads and MPM2 antibody bound to protein-G beads were incubated with the peptide library mixtures and washed extensively. Bound peptides were eluted with 30% acetic acid and sequenced.

The chromogenic oligopeptides were synthesized (A. Bernhardt, M. Drewello, & M. Schutkowski, *Int. J. Peptide Protein Res.* 50:143 (1997)) and confirmed by NMR. Standard peptides were purchased from Bachem. PPIase activity were assayed and the bimolecular rate constants $k_{cat}/K_m$ were calculated according to the equation $k_{cat}/K_m=(k_{obs}-k_u)/[\text{PPIase}]$, where $k_u$ is the first-order rate constant for spontaneous cis/trans isomerization and $k_{obs}$ is the pseudo-first-order rate constant for cis/trans isomerization in the presence of PPIase, as described in G. Fischer, H. Bang, C. Mech, *Biomed. Biochim. Acta* 43:1101 (1984); J. L. Kofron et al. *Biochemistry* 30:6127 (1991). Affinity of Pin1 for peptides was measured as described in Schutkowski, M., Wöllner, S., & Fischer, G. *Biochemistry* 34:13016, (1995).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

---

What is claimed is:

1. An inhibitor of a phosphoserine- or phosphothreonine-proline specific peptidyl-prolyl isomerase comprising a peptide or peptide mimetic wherein the peptide or peptide mimetic comprises two to ten amino acids and wherein the inhibitor has a core moiety having a formula:

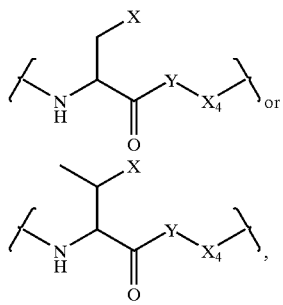

wherein:

x is a negatively charged tetra or pentavalent moiety;

$X_4$ is Arg or an aromatic amino acid; and

Y is Pro or a Pro analog represented by one of the following structural formulas:
wherein:

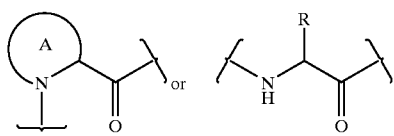

ring A is a 4 to 7-membered substituted or unsubstituted heterocyclic group; and R is selected from the group consisting of imidazolyl, pyrrolyl, tropolonyl, phenyl and camphoryl.

2. The inhibitor of claim 1 wherein x is selected from the group consisting of $-OPO_3^{2-}$, $-PO_3^{2-}$, $-OSO_3^{2-}$ and $-OBO_2^{2-}$.

3. The inhibitor of claim 1 wherein the $K_i$ of the inhibitor is ten micromolar or less.

4. The compound of claim 1 wherein the peptide or peptide mimetic is linear.

5. The inhibitor of claim 1, the peptide or peptide mimetic is represented by the following formula:

$X_1$-$X_2$-$X_3$-pS-P-$X_4$-$X_5$-$X_6$ wherein:

pS is phosphorylated serine;

P is proline;

$X_1$ is Trp, Tyr, or Phe;

$X_2$ is Phe or Ile;

$X_3$ and $X_4$ are Tyr, Arg, Phe or Trp;

$X_5$ is Leu or Ile; and $X_6$ is any amino acid.

6. A peptide inhibitor of a phosphoserine- or phosphothreonine-proline-specific peptide prolyl isomerase consisting of Trp-Phe-Tyr-pSer-Pro-Arg (SEQ ID NO:25).

7. A composition comprising an acceptable carrier and a compound according to claim 1 in an amount effective to inhibit peptidyl/proline isomerase.

8. A method of inhibiting growth of a cell comprising contacting the cell with the peptidyl prolyl isomerase inhibitor of claim 1 for a time and under conditions effective to inhibit growth of said cell.

9. The method of claim 8 wherein the peptidyl-prolyl isomerase is Pin1.

10. The method of claim 8 wherein the cell is in a human.

11. The method of claim 8 wherein the cell growth results from a hyperplastic disorder.

12. The method of claim 8 wherein the cell is a eukaryotic cells.

13. The method of claim 8 where the cell is a mammalian cell.

14. The inhibitor of a phosphoserine- or phosphothreonine-proline specific peptidyl-prolyl isomerase of claim 1, wherein the phosphoserine- or phosphothreonine- proline specific peptidyl-prolyl isomerase is Pin1, wherein "Pin1" is an abbreviation for "protein interacting with NIMA", the protein product of the *nim*A gene of the fungus *Asperigillus nidulans*.

15. The compound of claim 1 wherein the peptide or peptide mimetic is cyclic.

16. The method of claim 8 wherein the cell growth results from a neoplastic disorder.

17. The composition of claim 7, wherein the peptidyl-proline isomerase is Pin1.

18. The method of claim 8 where the cell is a yeast cell.

19. The method of claim 8 where the cell is a fungal cell.

* * * * *

UNITED STATES PATENT AND TRADEMARK OFFICE
CERTIFICATE OF CORRECTION

PATENT NO.    : 6,462,173 B1
DATED         : October 8, 2002
INVENTOR(S)   : Lu et al.

It is certified that error appears in the above-identified patent and that said Letters Patent is hereby corrected as shown below:

Column 46,
Line 41, after the comma please insert -- wherein --.
Line 60, please delete "peptidyl/proline" and insert -- peptidyl-proline --.
Line 66, after "Pin 1" please insert -- , wherein "Pin1" is an abbreviation for "protein interacting with NIMA", the protein product of the *nimA* gene of the fungus *Asperigillus nidulans* --.

Column 47,
Line 4, please delete "cells" and insert -- cell --.
Lines 11, 12 and 13, after "Pin 1" please delete ", wherein "Pin1" is an abbreviation for "protein interacting with NIMA", the protein product of the *nimA* gene of the fungus *Asperigillus nidulans*".

Signed and Sealed this

Third Day of June, 2003

JAMES E. ROGAN
*Director of the United States Patent and Trademark Office*